United States Patent
Buras

(10) Patent No.: US 7,657,310 B2
(45) Date of Patent: Feb. 2, 2010

(54) TREATMENT OF REPRODUCTIVE ENDOCRINE DISORDERS BY VAGUS NERVE STIMULATION

(75) Inventor: William R. Buras, Friendswood, TX (US)

(73) Assignee: Cyberonics, Inc., Houston, TX (US)

( * ) Notice: Subject to any disclaimer, the term of this patent is extended or adjusted under 35 U.S.C. 154(b) by 17 days.

(21) Appl. No.: 11/340,309

(22) Filed: Jan. 26, 2006

(65) Prior Publication Data
US 2007/0173891 A1   Jul. 26, 2007

(51) Int. Cl.
*A61N 1/00* (2006.01)
(52) U.S. Cl. ......................................... 607/2
(58) Field of Classification Search ................ 607/2, 607/3, 45, 116, 118, 39, 46
See application file for complete search history.

(56) References Cited

U.S. PATENT DOCUMENTS

| | | |
|---|---|---|
| 3,796,221 A | 3/1974 | Hagfors |
| 4,305,402 A | 12/1981 | Katims |
| 4,338,945 A | 7/1982 | Kosugi et al. |
| 4,424,812 A | 1/1984 | Lesnick |
| 4,431,000 A | 2/1984 | Butler et al. |
| 4,459,989 A | 7/1984 | Borkan |
| 4,503,863 A | 3/1985 | Katims |
| 4,541,432 A | 9/1985 | Molina-Negro et al. |
| 4,573,481 A | 3/1986 | Bullara |
| 4,590,946 A | 5/1986 | Loeb |
| 4,592,339 A | 6/1986 | Kuzmak et al. |
| 4,612,934 A | 9/1986 | Borkan |
| 4,702,254 A | 10/1987 | Zabara |
| 4,793,353 A | 12/1988 | Borkan |
| 4,865,048 A | 9/1989 | Eckerson |
| 4,867,164 A | 9/1989 | Zabara |
| 4,909,263 A * | 3/1990 | Norris .................... 607/39 |
| 4,920,979 A | 5/1990 | Bullara |
| 5,025,807 A | 6/1991 | Zabara |
| 5,074,868 A | 12/1991 | Kuzmak |
| 5,154,172 A | 10/1992 | Terry, Jr. et al. |
| 5,179,950 A | 1/1993 | Stanislaw |
| 5,186,170 A | 2/1993 | Varrichio et al. |
| 5,188,104 A | 2/1993 | Wernicke et al. |

(Continued)

FOREIGN PATENT DOCUMENTS

EP   1145736   10/2001

(Continued)

OTHER PUBLICATIONS

PCT/US2007/000342 Search Report (Aug. 30, 2007).

(Continued)

*Primary Examiner*—George Manuel
(74) *Attorney, Agent, or Firm*—Williams, Morgan & Amerson P.C.; Timothy L. Scott

(57) ABSTRACT

I disclose a method of treating a reproductive endocrine disorder in a patient, including coupling at least one electrode to at least one portion of a cranial nerve of the patient; and applying an electrical signal to said cranial nerve using said electrode to treat said reproductive endocrine disorder. Among the reproductive endocrine disorders which may be treated by the method are gonadal dysgenesis, hypogonadism, hypergonadism, delayed puberty, amenorrhea, infertility, premature menopause, and polycystic ovarian disease.

22 Claims, 11 Drawing Sheets

U.S. PATENT DOCUMENTS

| | | |
|---|---|---|
| 5,194,426 A | 3/1993 | DaVanzo et al. |
| 5,199,430 A | 4/1993 | Fang et al. |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,226,429 A | 7/1993 | Kuzmak |
| 5,231,988 A | 8/1993 | Wernicke et al. |
| 5,235,980 A | 8/1993 | Varrichio et al. |
| 5,237,991 A | 8/1993 | Baker, Jr. et al. |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,311,876 A | 5/1994 | Olsen et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,423,872 A | 6/1995 | Cigaina |
| 5,501,702 A | 3/1996 | Plicchi et al. |
| 5,514,175 A | 5/1996 | Kim et al. |
| 5,540,730 A | 7/1996 | Terry, Jr. et al. |
| 5,540,734 A | 7/1996 | Zabara |
| 5,571,150 A | 11/1996 | Wernicke et al. |
| 5,601,604 A | 2/1997 | Vincent |
| 5,611,350 A | 3/1997 | John |
| 5,645,570 A | 7/1997 | Corbucci |
| 5,665,706 A | 9/1997 | DaVanzo et al. |
| 5,690,681 A | 11/1997 | Geddes et al. |
| 5,690,688 A | 11/1997 | Noren et al. |
| 5,690,691 A | 11/1997 | Chen et al. |
| 5,700,282 A | 12/1997 | Zabara |
| 5,702,428 A | 12/1997 | Tippey et al. |
| 5,707,400 A | 1/1998 | Terry, Jr. et al. |
| 5,743,860 A | 4/1998 | Hively et al. |
| 5,771,903 A | 6/1998 | Jakobsson |
| 5,792,212 A | 8/1998 | Weijand |
| 5,836,994 A | 11/1998 | Bourgeois |
| 5,861,014 A | 1/1999 | Familoni |
| 5,913,882 A | 6/1999 | King |
| 5,916,239 A | 6/1999 | Geddes et al. |
| 5,919,216 A | 7/1999 | Houben et al. |
| 5,928,272 A | 7/1999 | Adkins et al. |
| 5,935,099 A | 8/1999 | Peterson et al. |
| 5,978,702 A | 11/1999 | Ward et al. |
| 5,995,868 A | 11/1999 | Dorfmeister et al. |
| 5,995,872 A | 11/1999 | Bourgeois |
| 6,009,877 A | 1/2000 | Edwards |
| 6,024,539 A | 2/2000 | Blomquist |
| 6,026,326 A | 2/2000 | Bardy |
| 6,041,258 A | 3/2000 | Cigaina et al. |
| 6,044,846 A | 4/2000 | Edwards |
| 6,083,249 A | 7/2000 | Familoni |
| 6,091,992 A | 7/2000 | Bourgeois et al. |
| 6,092,528 A | 7/2000 | Edwards |
| 6,102,922 A | 8/2000 | Jakobsson et al. |
| 6,104,955 A | 8/2000 | Bourgeois |
| 6,104,956 A | 8/2000 | Naritoku et al. |
| 6,109,269 A | 8/2000 | Rise et al. |
| 6,115,635 A | 9/2000 | Bourgeois |
| 6,128,538 A | 10/2000 | Fischell et al. |
| 6,129,685 A | 10/2000 | Howard, III |
| 6,161,044 A | 12/2000 | Silverstone |
| 6,167,311 A | 12/2000 | Rezai |
| 6,178,349 B1 | 1/2001 | Kieval |
| 6,181,965 B1 | 1/2001 | Loeb et al. |
| 6,205,359 B1 | 3/2001 | Boveja |
| 6,216,039 B1 | 4/2001 | Bourgeois |
| 6,233,488 B1 | 5/2001 | Hess |
| 6,238,423 B1 | 5/2001 | Bardy |
| 6,240,316 B1 | 5/2001 | Richmond et al. |
| 6,241,704 B1 | 6/2001 | Peterson et al. |
| 6,243,607 B1 | 6/2001 | Mintchev et al. |
| 6,269,270 B1 | 7/2001 | Boveja |
| 6,295,472 B1 | 9/2001 | Rubinstein et al. |
| 6,304,775 B1 | 10/2001 | Iasemidis et al. |
| 6,321,124 B1 | 11/2001 | Cigaina |
| 6,327,503 B1 | 12/2001 | Familoni |
| 6,337,997 B1 | 1/2002 | Rise |
| 6,339,725 B1 | 1/2002 | Naritoku et al. |
| 6,341,236 B1 | 1/2002 | Osorio et al. |
| 6,356,784 B1 | 3/2002 | Lozano et al. |
| 6,356,786 B1 | 3/2002 | Rezai et al. |
| 6,356,787 B1 | 3/2002 | Rezai et al. |
| 6,356,788 B2 | 3/2002 | Boveja |
| 6,366,814 B1 | 4/2002 | Boveja et al. |
| 6,374,140 B1 | 4/2002 | Rise |
| 6,381,495 B1 | 4/2002 | Jenkins |
| 6,418,344 B1 | 7/2002 | Rezai et al. |
| 6,425,852 B1 | 7/2002 | Epstein et al. |
| 6,429,217 B1 | 8/2002 | Puskas |
| 6,438,423 B1 | 8/2002 | Rezai et al. |
| 6,449,512 B1 | 9/2002 | Boveja |
| 6,463,328 B1 | 10/2002 | John |
| 6,466,822 B1 | 10/2002 | Pless |
| 6,473,644 B1 | 10/2002 | Terry, Jr. et al. |
| 6,477,418 B2 | 11/2002 | Plicchi et al. |
| 6,477,423 B1 | 11/2002 | Jenkins |
| 6,484,132 B1 | 11/2002 | Hively et al. |
| 6,505,074 B2 | 1/2003 | Boveja et al. |
| 6,532,388 B1 | 3/2003 | Hill et al. |
| 6,535,764 B2 | 3/2003 | Imran et al. |
| 6,542,776 B1 | 4/2003 | Gordon et al. |
| 6,549,804 B1 | 4/2003 | Osorio et al. |
| 6,556,868 B2 | 4/2003 | Naritoku et al. |
| 6,560,486 B1 | 5/2003 | Osorio et al. |
| 6,564,102 B1 | 5/2003 | Boveja |
| 6,571,125 B2 | 5/2003 | Thompson |
| 6,587,719 B1 * | 7/2003 | Barrett et al. .................. 607/2 |
| 6,587,726 B2 | 7/2003 | Lurie et al. |
| 6,587,727 B2 | 7/2003 | Osorio et al. |
| 6,591,137 B1 | 7/2003 | Fischell et al. |
| 6,591,138 B1 | 7/2003 | Fischell et al. |
| 6,600,953 B2 | 7/2003 | Flesler et al. |
| 6,600,956 B2 | 7/2003 | Maschino et al. |
| 6,606,518 B1 | 8/2003 | Cigaina |
| 6,606,523 B1 | 8/2003 | Jenkins |
| 6,609,025 B2 | 8/2003 | Barrett et al. |
| 6,609,030 B1 | 8/2003 | Rezai et al. |
| 6,610,713 B2 | 8/2003 | Tracey |
| 6,611,715 B1 | 8/2003 | Boveja |
| 6,612,983 B1 | 9/2003 | Marchal |
| 6,615,081 B1 | 9/2003 | Boveja |
| 6,615,084 B1 | 9/2003 | Cigaina |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,631,296 B1 | 10/2003 | Parramon et al. |
| 6,635,014 B2 | 10/2003 | Starkweather et al. |
| 6,647,296 B2 | 11/2003 | Fischell et al. |
| 6,650,943 B1 | 11/2003 | Whitehurst et al. |
| 6,656,125 B2 | 12/2003 | Misczynski et al. |
| 6,662,052 B1 | 12/2003 | Sarwal et al. |
| 6,671,555 B2 | 12/2003 | Gielen et al. |
| 6,671,556 B2 | 12/2003 | Osorio et al. |
| 6,684,104 B2 | 1/2004 | Gordon et al. |
| 6,684,105 B2 | 1/2004 | Cohen et al. |
| 6,694,191 B2 | 2/2004 | Starkweather et al. |
| 6,721,603 B2 | 4/2004 | Zabara et al. |
| 6,735,474 B1 | 5/2004 | Loeb et al. |
| 6,735,475 B1 | 5/2004 | Whitehurst et al. |
| 6,754,536 B2 | 6/2004 | Swoyer et al. |
| 6,760,626 B1 | 7/2004 | Boveja |

| | | |
|---|---|---|
| 6,768,969 B1 | 7/2004 | Nikitin et al. |
| 6,775,573 B2 | 8/2004 | Schuler et al. |
| 6,788,970 B1 | 9/2004 | Park et al. |
| 6,788,975 B1 | 9/2004 | Whitehurst et al. |
| 6,793,670 B2 | 9/2004 | Osorio et al. |
| 6,819,956 B2 | 11/2004 | DiLorenzo |
| 6,826,428 B1 | 11/2004 | Chen et al. |
| 6,832,114 B1 | 12/2004 | Whitehurst et al. |
| 6,853,862 B1 | 2/2005 | Marchal et al. |
| 6,885,888 B2 | 4/2005 | Rezai |
| 6,889,076 B2 | 5/2005 | Cigaina |
| 6,895,278 B1 | 5/2005 | Gordon |
| 6,904,390 B2 | 6/2005 | Nikitin et al. |
| 6,908,487 B2 | 6/2005 | Cigaina |
| 6,920,357 B2 | 7/2005 | Osorio et al. |
| 6,922,592 B2 | 7/2005 | Thompson et al. |
| 6,934,580 B1 | 8/2005 | Osorio et al. |
| 6,944,501 B1 | 9/2005 | Pless |
| 6,959,215 B2 | 10/2005 | Gliner et al. |
| 6,961,618 B2 | 11/2005 | Osorio et al. |
| 7,006,859 B1 | 2/2006 | Osorio et al. |
| 7,054,792 B2 | 5/2006 | Frei et al. |
| 7,079,977 B2 | 7/2006 | Osorio et al. |
| 7,139,677 B2 | 11/2006 | Hively |
| 7,146,211 B2 | 12/2006 | Frei et al. |
| 7,146,218 B2 | 12/2006 | Esteller et al. |
| 7,149,572 B2 | 12/2006 | Frei et al. |
| 7,164,941 B2 | 1/2007 | Misczynski et al. |
| 7,167,743 B2 | 1/2007 | Heruth et al. |
| 7,167,750 B2 | 1/2007 | Knudson et al. |
| 7,171,271 B2 | 1/2007 | Koh et al. |
| 7,174,206 B2 | 2/2007 | Frei et al. |
| 7,177,678 B1 | 2/2007 | Osorio et al. |
| 7,188,053 B2 | 3/2007 | Nikitin et al. |
| 7,204,833 B1 | 4/2007 | Osorio et al. |
| 7,209,787 B2 | 4/2007 | DiLorenzo |
| 7,231,254 B2 | 6/2007 | DiLorenzo |
| 7,242,983 B2 | 7/2007 | Frei et al. |
| 7,242,984 B2 | 7/2007 | DiLorenzo |
| 7,254,439 B2 | 8/2007 | Misczynski et al. |
| 7,263,467 B2 | 8/2007 | Sackellares et al. |
| 7,277,758 B2 | 10/2007 | DiLorenzo |
| 7,280,867 B2 | 10/2007 | Frei et al. |
| 7,282,030 B2 | 10/2007 | Frei et al. |
| 7,289,844 B2 | 10/2007 | Misczynski et al. |
| 7,305,268 B2 | 12/2007 | Gliner et al. |
| 7,321,837 B2 | 1/2008 | Osorio et al. |
| 7,324,851 B1 | 1/2008 | DiLorenzo |
| 7,346,391 B1 | 3/2008 | Osorio et al. |
| 7,353,064 B2 | 4/2008 | Gliner et al. |
| 7,373,199 B2 | 5/2008 | Sackellares et al. |
| 7,389,144 B1 | 6/2008 | Osorio et al. |
| 7,401,008 B2 | 7/2008 | Frei et al. |
| 7,403,820 B2 | 7/2008 | DiLorenzo |
| 7,437,196 B2 | 10/2008 | Wyler et al. |
| 2002/0099417 A1 | 7/2002 | Naritoku et al. |
| 2002/0116030 A1 | 8/2002 | Rezai |
| 2002/0188214 A1 | 12/2002 | Misczynski et al. |
| 2003/0208212 A1 | 11/2003 | Cigaina |
| 2004/0153129 A1 | 8/2004 | Pless et al. |
| 2004/0167583 A1 | 8/2004 | Knudson et al. |
| 2004/0172085 A1 | 9/2004 | Knudson et al. |
| 2004/0176812 A1 | 9/2004 | Knudson et al. |
| 2004/0249416 A1 | 12/2004 | Yun et al. |
| 2005/0004621 A1 | 1/2005 | Boveja et al. |
| 2005/0010262 A1 | 1/2005 | Rezai et al. |
| 2005/0021092 A1 | 1/2005 | Yun et al. |
| 2005/0021103 A1 | 1/2005 | DiLorenzo |
| 2005/0021104 A1 | 1/2005 | DiLorenzo |
| 2005/0038484 A1 | 2/2005 | Knudson et al. |
| 2005/0049655 A1 | 3/2005 | Boveja et al. |
| 2005/0065562 A1 | 3/2005 | Rezai |
| 2005/0065573 A1 | 3/2005 | Rezai |
| 2005/0065574 A1* | 3/2005 | Rezai .................. 607/45 |
| 2005/0065575 A1 | 3/2005 | Dobak |
| 2005/0075702 A1 | 4/2005 | Shafer |
| 2005/0119703 A1 | 6/2005 | DiLorenzo |
| 2005/0124901 A1 | 6/2005 | Misczynski et al. |
| 2005/0131467 A1 | 6/2005 | Boveja |
| 2005/0131485 A1 | 6/2005 | Knudson et al. |
| 2005/0131486 A1 | 6/2005 | Boveja et al. |
| 2005/0143786 A1 | 6/2005 | Boveja |
| 2005/0143788 A1 | 6/2005 | Yun et al. ............... 607/46 |
| 2005/0154425 A1 | 7/2005 | Boveja et al. |
| 2005/0187590 A1 | 8/2005 | Boveja et al. |
| 2005/0192644 A1 | 9/2005 | Boveja et al. |
| 2006/0009815 A1 | 1/2006 | Boveja et al. |
| 2006/0069322 A1 | 3/2006 | Zhang et al. |
| 2006/0074450 A1 | 4/2006 | Boveja et al. |
| 2006/0079936 A1 | 4/2006 | Boveja et al. |
| 2006/0079945 A1 | 4/2006 | Libbus |
| 2006/0085046 A1 | 4/2006 | Rezai et al. |
| 2006/0106431 A1 | 5/2006 | Wyler et al. |
| 2006/0135877 A1 | 6/2006 | Giftakis et al. |
| 2006/0135881 A1 | 6/2006 | Giftakis et al. |
| 2006/0155495 A1 | 7/2006 | Osorio et al. |
| 2006/0161459 A9 | 7/2006 | Rosenfeld et al. |
| 2006/0167497 A1* | 7/2006 | Armstrong et al. ......... 607/2 |
| 2006/0212091 A1 | 9/2006 | Lozano et al. |
| 2006/0224191 A1 | 10/2006 | Dilorenzo |
| 2006/0241697 A1 | 10/2006 | Libbus et al. |
| 2006/0253168 A1 | 11/2006 | Wyler et al. |
| 2006/0253169 A1 | 11/2006 | Wyler et al. |
| 2006/0253170 A1 | 11/2006 | Wyler et al. |
| 2006/0253171 A1 | 11/2006 | Wyler et al. |
| 2006/0259095 A1 | 11/2006 | Wyler et al. |
| 2006/0293720 A1 | 12/2006 | DiLorenzo |

FOREIGN PATENT DOCUMENTS

| | | |
|---|---|---|
| WO | 9302744 | 2/1993 |
| WO | 9417771 | 8/1994 |
| WO | 2004064918 | 8/2004 |
| WO | WO2004/110551 | 12/2004 |
| WO | 2005007120 | 1/2005 |
| WO | 2005007232 | 1/2005 |
| WO | 2005053788 | 6/2005 |
| WO | 2006050144 | 5/2006 |
| WO | 2006122148 | 11/2006 |

OTHER PUBLICATIONS

Kriwanek, S., et al.; "Therapeutic Failures After Gastric Bypass Operations Pot Morbid Obesity," Langenbecks Archiv Fur Chirurgie, 38(2): 70-74, 1995.

Grundy et al., "Sensory Afferents From The Gastrointestinal Tract" Chapter 16, Handbook of Physiology of Abdominal Vagal Afferents, Chapter 12, CRC Press, New York, NY, 1992.

"External Sensory Events and the Control of the Gastrointestinal Tract: An Introduction," Neuroanatomy and Physiology of Abdominal Vagal Afferents, Chapter 5. CRC Press, New York, NY, 1992.

Leibowitz, S.F., "Central Physiological Determinants of Eating Behavior and Weight" Eating Disorders and Obesity: A Comprehensive Handbook, Ch. 1, Brownell and Fairburn. Ed.. The Guilford Press, 1995.

Woodbury, et al., "Vagal Stimulation Reduces the Severity Of Maximal Electroshock Seizures in Intact Rats. Use of a Cuff Electrode for Stimulating And Recording"; Pacing and Clinical Electrophysiology, vol. 14 (Jan. 1991), pp. 94-107.

Zabara, Jacob; "Inhibition Of Experimental Seizures In Canines By Repetitive Vagal Stimulation;" Epilepsia, vol. 33 (6) (1992), pp. 1005-1012.

Hallowitz et al., "Effects Of Vagal Volleys On Units Of Intralaminar and Juxtalaminar Thalamic Nuclei in Monkeys;" Brain Research, vol. 130 (1977), pp. 271-286.

Bachman, D.,S. et al.; "Effects Of Vagal Volleys And Serotonin On Units Of Cingulate Cortex in Monkeys;" Brain Research, vol. 130 (1977). pp. 253-269.

Clark, K.B., et al.; "Enhanced Recognition Memory Following Vagus Nerve Stimulation in Human Subjects;" Nature Neuroscience, vol. 2, No. 1, (Jan. 1999) pp. 93-98.

Klapper, M.D., et al., "VNS Therapy Shows Potential Benefit in Patients with Migraine and Chronic Daily Headache After 3 to 6 Months of Treatment (Preliminary Results)" 45th Annual Scientific Meeting of the American Headache Society (Jun. 2003).

Ritter, S., et al.; "Participation of Vagal Sensory Neurons in Putative Satiety Signals from the Upper Gastroinstestinal Tract" Neuroanatomy and Physiology of Abdominal Vagal Afferents, Ch. 10 (1992); pp. 222-248.

Rogers, R.C., et al.; "Central Regulation of Brainstem Gastric Vago-Vagal Control Circuits" Neuroanatomy and Physiology of Abdominal Vagal Afferents, Ch. 5 (1992); pp. 100-134.

Smith, D.C., et al.; "Electrical Stimulation of the Vagus Nerve Enhances Cognitive and Motor Recovery Following Moderate Fluid Percussion Injury in the Rat" Journal of Neurotrauma, vol. 22, No. 12, (2005) pp. 1485-1502.

Tubbs, R.S., et al.; "Left-Sided Vagus Nerve Stimulation Decreases Intracranial Pressure Without Resultant Bradycardia in the Pig: A Potential Therapeutic Modality for Humans" Child's Nervous System Original Paper; Springer-Verlag 2004.

Zabara, J.; "Neuroinhibition in the Regulation of Emesis" Mechanisms and Control of Emesis, vol. 223, (1992) pp. 285-295.

Zabara, J.; "Neuroinhibition of Xylaine Induced Emesis" Pharmacology & Toxicology, vol. 63 (1988) pp. 70-74.

Zabara, J., et al.; "15.11 Reciprocal Inhibition in Vomiting" The Physiologist, vol. 28, No. 4 (1985) p. 275.

Zabara, J., et al.; "Neuroinhibition in the Regulation of Emesis" Space Life Sciences, vol. 3 (1972) pp. 282-292.

* cited by examiner

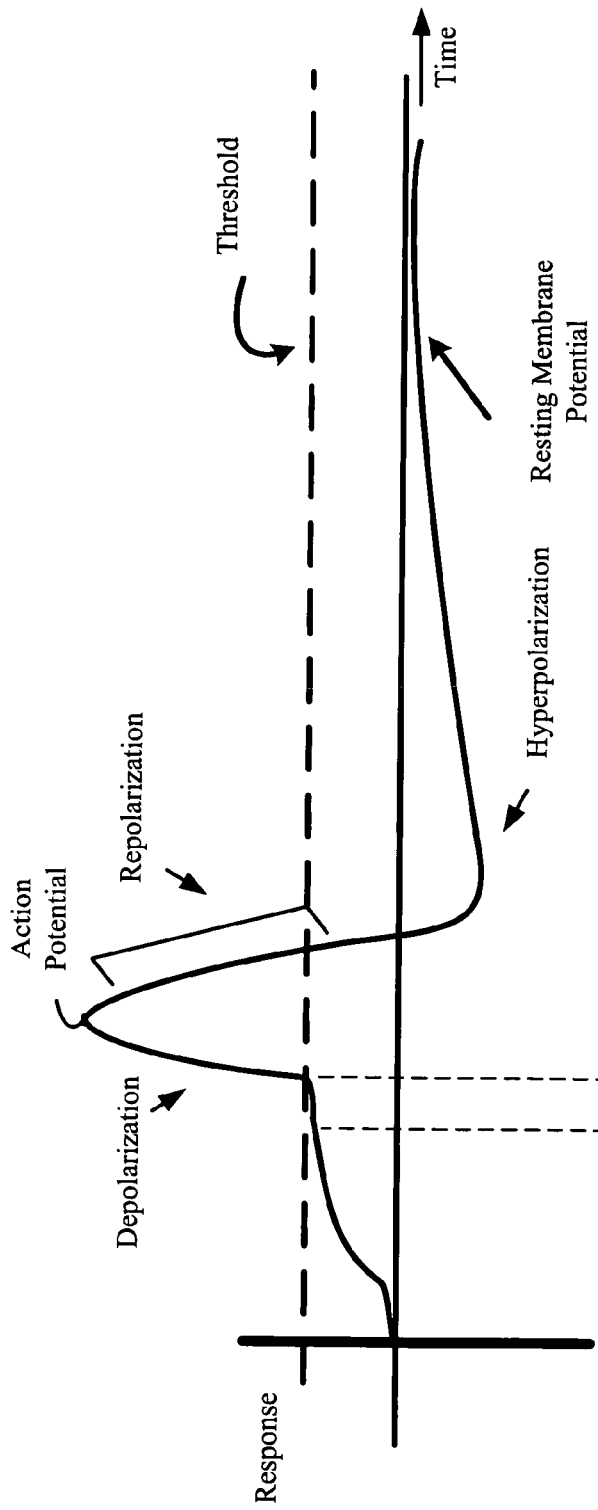
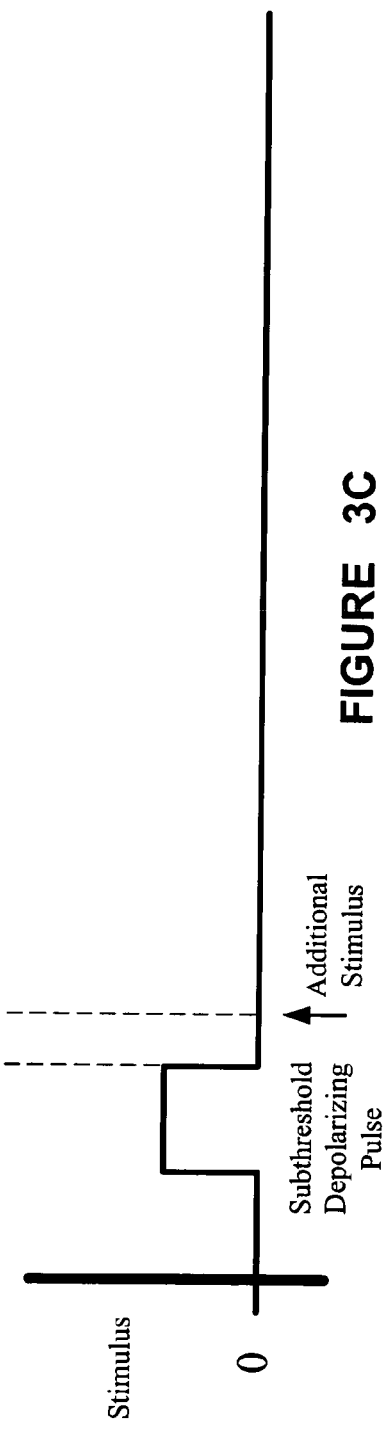
FIGURE 3B
FIGURE 3C

TREATMENT OF REPRODUCTIVE ENDOCRINE DISORDERS BY VAGUS NERVE STIMULATION

BACKGROUND OF THE INVENTION

1. Field of the Invention

The present invention relates generally to methods and apparatus for treating disorders by cranial nerve stimulation. More particularly, it concerns methods and apparatus for treating reproductive endocrine disorders by vagus nerve stimulation.

2. Description of Related Art

The human nervous system (HNS) includes the brain and the spinal cord, collectively known as the central nervous system (CNS). The central nervous system comprises nerve fibers. The network of nerves in the remaining portions of the human body forms the peripheral nervous system (PNS). Some peripheral nerves, known as cranial nerves, connect directly to the brain to control various brain functions, such as vision, eye movement, hearing, facial movement, and feeling. Another system of peripheral nerves, known as the autonomic nervous system (ANS), controls blood vessel diameter, intestinal movements, and actions of many internal organs. Autonomic functions include blood pressure, body temperature, heartbeat and essentially all the unconscious activities that occur without voluntary control.

Like the rest of the human nervous system, nerve signals travel up and down the peripheral nerves, which link the brain to the rest of the human body. Nerves are typically composed of many individual nerve fibers, which may be of several different types. Some (but not all) nerve fibers in the brain and the peripheral nerves are sheathed in a covering called myelin, which insulates electrical pulses traveling along the nerves. A nerve bundle may comprise up to 100,000 or more individual nerve fibers of different types, including larger diameter A and B fibers which comprise a myelin sheath and C fibers which have a much smaller diameter and are unmyelinated. Different types of nerve fibers, among other things, comprise different sizes, conduction velocities, stimulation thresholds, and myelination status (i.e., myelinated or unmyelinated).

Normal reproductive function depends on complex hormonal communication between the endocrine system and target organs whose functions are regulated by the endocrine system. Normal function is essential to sexual development at puberty and to the cyclic processes of ovulation and menstruation.

The hypothalamus secretes a small peptide, gonadotropin-releasing hormone (GnRH), also known as luteinizing hormone-releasing hormone, which regulates release of the gonadotropins luteinizing hormone (LH) and follicle-stimulating hormone (FSH) from the anterior pituitary gland. LH and FSH promote maturation of gametes and stimulate secretion of sex hormones such as estrogen and testosterone from the gonads. Estrogen and progesterone stimulate various organs of the reproductive system (e.g., breasts, uterus, and vagina) and exert negative and positive feedback effects on the CNS-hypothalamic-pituitary unit, inhibiting and stimulating gonadotropin secretion.

Virtually all hormones are released in short bursts or pulses at intervals of 1 to 3 hr.

LH and FSH are elevated at birth but fall to low levels within a few months and remain low throughout the prepubertal years, with FSH generally slightly higher than LH. The adrenal androgens dehydroepiandrosterone (DHEA) and DHEA sulfate begin to increase several years before puberty. These increases may be important in initiating pubic and axillary hair growth (adrenarche) and other pubertal events.

The mechanisms initiating puberty are not entirely clear. Central influences may inhibit the pulsatile release of GnRH during childhood, then initiate its release to induce puberty early in adolescence. Impairment of these mechanisms may result in delayed puberty.

Variations in hormonal levels are also involved in the menstrual cycle. The follicular (preovulatory) phase of the menstrual cycle extends from the first day of menses to the day before the preovulatory LH surge. During the first half of this phase, FSH secretion is increased slightly, stimulating growth of a cohort of 3 to 30 follicles that have been recruited for accelerated growth during the last days of the preceding cycle. As FSH levels decline, one of the recruited follicles is selected for ovulation; it matures, and the others undergo atresia. Circulating LH levels rise slowly, beginning 1 to 2 days after the increase in FSH. Estrogen and progesterone secretion by the ovaries is relatively constant and remains low early in this phase.

About 7 to 8 days before the LH surge, ovarian secretion of estrogen, particularly of estradiol, by the selected follicle increases slowly at first, then accelerates, generally peaking on the day before the LH surge. The rise in estrogen is accompanied by a slow but steady increase in LH and a decrease in FSH levels. LH and FSH levels may diverge because FSH secretion is preferentially inhibited by estrogens (compared with LH secretion) and is specifically inhibited by inhibin. Just before the LH surge, progesterone levels also begin to increase significantly.

In the ovulatory phase, a series of complex endocrine events culminates in the LH surge—the massive preovulatory release of LH by the pituitary gland. The LH surge results in part from positive estrogen feedback. A smaller increase in FSH secretion occurs simultaneously, but its significance is not understood. As LH levels increase, estradiol levels decrease, but progesterone levels continue to increase. The LH surge typically lasts 36 to 48 hr and consists of multiple large bursts of LH released in pulses. The LH surge, which results in complete maturation of the follicle, is necessary for ovulation—release of the ovum from the mature graafian follicle—which usually occurs 16 to 32 hr after onset of the surge. The mechanism of ovulation is unclear.

During the menstrual cycle, the pulsatile secretion of LH and FSH is determined by the pulsatile secretion of GnRH. The frequency and amplitude of the LH and FSH pulses are modulated by ovarian hormones and vary throughout the menstrual cycle. No separate releasing hormone for FSH has been identified. Evidence suggests that the same cells sometimes contain LH and FSH, so differential release of LH and FSH must result from interactions of various factors (e.g., GnRH, estradiol, inhibin). Also, the disparate half-lives of LH (20 to 30 min) and FSH (2 to 3 hr) affect circulating levels.

Impairment of normal hormonal activity at various stages of the menstrual cycle can result in amenorrhea or infertility, among other ailments. Chronic impairment of normal hormonal activity can result in premature menopause.

Changes in levels of reproductive hormones can also lead to disorders after a person's reproductive years have ended. Reduction in estrogen levels in postmenopausal women can lead to osteoporosis, a weakening of the bones that can lead to a greater incidence of fracture and subsequent decrease in quality of life.

SUMMARY OF THE INVENTION

In one embodiment, the present invention relates to a method of treating a patient having a reproductive endocrine disorder including coupling at least one electrode to at least one vagus nerve of the patient and applying an electrical signal to the vagus nerve using the electrode to treat the reproductive endocrine disorder.

In another embodiment, the present invention relates to a method of treating a patient having a reproductive endocrine disorder including coupling at least one electrode to at least one vagus nerve of the patient, providing a programmable electrical signal generator coupled to the electrode, generating an electrical signal with the electrical signal generator, and applying the electrical signal to the electrode to treat the reproductive endocrine disorder.

In another embodiment, the present invention relates to a computer readable program storage device encoded with instructions that, when executed by a computer, perform a method including generating an electrical signal and providing the electrical signal to a vagus nerve of the patient by using an electrode to treat a reproductive endocrine disorder.

In another embodiment, the present invention relates to a reproductive endocrine disorder treatment system including at least one electrode coupled to at least one vagus nerve of a patient and an implantable device operatively coupled to the electrode and comprising an electrical signal generator capable of applying an electrical signal to the vagus nerve using the electrode to treat the reproductive endocrine disorder.

BRIEF DESCRIPTION OF THE DRAWINGS

The invention may be understood by reference to the following description taken in conjunction with the accompanying drawings, in which like reference numerals identify like elements, and in which:

FIG. 3B illustrates an exemplary electrical signal response of a firing neuron as a graph of voltage at a given location at particular times during firing by the neurostimulator of FIG. 2, when applying a sub-threshold depolarizing pulse and additional stimulus to the vagus nerve, in accordance with one illustrative embodiment of the present invention;

FIG. 3C illustrates an exemplary stimulus including a sub-threshold depolarizing pulse and additional stimulus to the vagus nerve for firing a neuron as a graph of voltage at a given location at particular times by the neurostimulator of FIG. 2, in accordance with one illustrative embodiment of the present invention;

Figure 1:
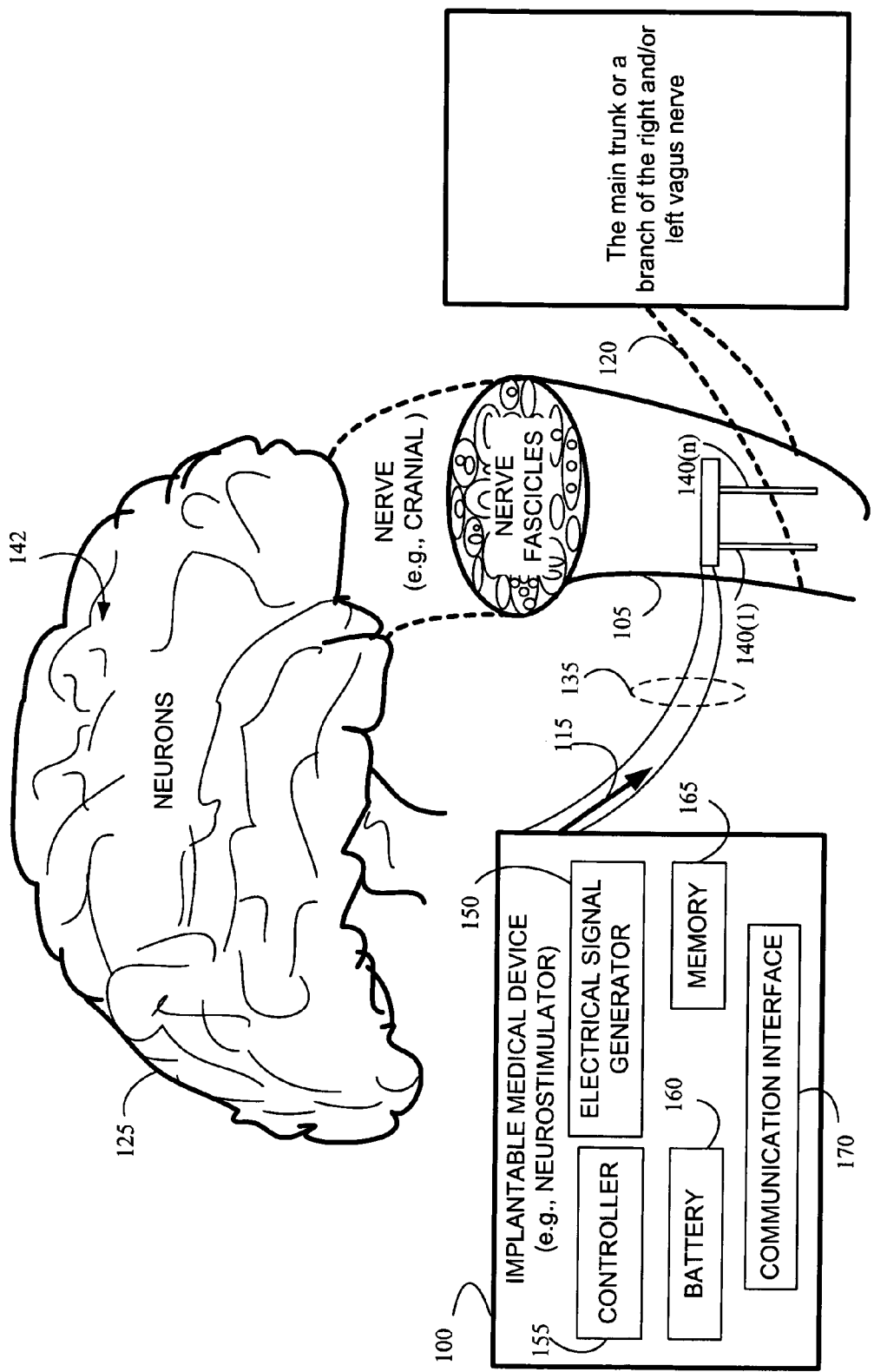
FIG. 1 is a stylized schematic representation of an implantable medical device that stimulates a cranial nerve for treating a patient with a reproductive endocrine disorder, according to one illustrative embodiment of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DESCRIPTION OF ILLUSTRATIVE EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

Certain terms are used throughout the following description and claims refer to particular system components. As one skilled in the art will appreciate, components may be referred to by different names. This document does not intend to distinguish between components that differ in name but not function. In the following discussion and in the claims, the terms "include" and "including" are used in an open-ended fashion, and thus should be interpreted to mean "including, but not limited to." Also, the term "couple" or "couples" is intended to mean either a direct or an indirect electrical connection. For example, if a first device couples to a second device, that connection may be through a direct electrical connection or through an indirect electrical connection via other devices, biological tissues, or magnetic fields. "Direct contact," "direct attachment," or providing a "direct coupling" indicates that a surface of a first element contacts the surface of a second element with no substantial attenuating medium therebetween. The presence of substances, such as bodily fluids, that do not substantially attenuate electrical connections does not vitiate direct contact. "Transcutaneous contact" or variations thereof indicates that a surface of a first element contacts the skin of a patient and does not directly contact the surface of a second element on the other side of the skin of the patient. The word "or" is used in the inclusive sense (i.e., "and/or") unless a specific use to the contrary is explicitly stated.

Embodiments of the present invention provide for the treatment of reproductive endocrine disorder(s) by stimulation of cranial nerves, such as the vagus nerves, trigeminal nerves, accessory nerves, or hypoglossal nerves. Some embodiments of the present invention provide for an electrical stimulation of a portion of a cranial nerve to treat a reproductive endocrine disorder. Reproductive endocrine disorders may be treated using the electrical stimulation provided by an implantable medical device (IMD). In certain alternative embodiments, one or more components of the system may be external to the patient's body. Such alternative systems include partially implanted systems having an implantable electrode to which an external signal generator is coupled by radio frequency (RF) coupling, as well as fully external systems in which the electrode and signal generator are both located outside the body of the patient, providing transcutaneous stimulation of a target cranial nerve.

The human reproductive endocrine system refers to that part of the human endocrine system primarily involved in the development and function of the gonadal organs. In one embodiment, reproductive endocrine disorders refers to disorders that result from deranged or absent gonadal and/or pituitary hormonal signaling. Examples of disorders that may result from deranged or absent signaling are disorders in growth and structural integrity of the reproductive organs, disorders in sexual gamete production, disorders in sexual differentiation, disorders in patterns of sexual behavior, and disorders in reproductive function (ovulation, spermatogenesis, pregnancy, lactation, etc). Reproductive endocrine disorders may also include disorders and/or derangements of bodily systems not directly related to reproductive development and functioning, but which are influenced by hormones and related biochemical factors that are directly related to the aforementioned reproductive functions. Examples of these other influences are the effects of hormones (androgens, estrogens and progestogens) and gonadotropins on musculoskeletal development and maintenance, skin development and maintenance, cognition, mood, memory and behavior, and other functions indirectly related to reproduction.

Accordingly, specific reproductive endocrine disorders may include, without limitation, gonadal dysgenesis, hypogonadism, hypergonadism, delayed puberty, amenorrhea, infertility, premature menopause, or polycystic ovarian syndrome, osteoporosis, hirsutism, and sarcopenia. Some embodiments of the present invention provide for monitoring a feedback or biofeedback from a patient or an external source in response to a sensory signal. Based upon the feedback or biofeedback, an adjustment to subsequent stimulation may be performed.

Cranial nerve stimulation has been used to treat a number of nervous system disorders, including epilepsy and other movement disorders, depression and other neuropsychiatric disorders, dementia, coma, migraine headache, obesity, eating disorders, sleep disorders, cardiac disorders (such as congestive heart failure and atrial fibrillation), hypertension, non-reproductive endocrine disorders (such as diabetes and hypoglycemia), and pain, among others. See, e.g., U.S. Pats. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515, each of which is hereby incorporated by reference herein. Despite the recognition that cranial nerve stimulation may be an appropriate treatment for the foregoing conditions, the fact that detailed neural pathways for many (if not all) cranial nerves remain relatively unknown makes predictions of efficacy for any given disorder difficult. Even if such pathways were known, moreover, the precise stimulation parameters that would energize particular pathways that affect the particular disorder likewise are difficult to predict. Accordingly, cranial nerve stimulation, and particularly vagus nerve stimulation, has not heretofore been deemed appropriate for use in treating reproductive endocrine disorders.

In one embodiment of the present invention, methods, apparatus, and systems stimulate an autonomic nerve, such as a cranial nerve, e.g., a vagus nerve, using an electrical signal to treat a reproductive endocrine disorder. "Electrical signal" on the nerve refers to electrical activity (i.e., a pulsed or non-pulsed electrical current) that is applied to the nerve from a source external to the nerve, e.g., an implanted neurostimulator. In general, the term "electrical signal" thus refers to an exogenous electrical signal generated by the implanted medical device and applied to a nerve, in contrast to native electrical activity comprising afferent and efferent action potentials, hyperpolarizations, and sub-threshold depolarizations that are generated by the patient's body. Disclosed herein is a method for treating a reproductive endocrine disorder using stimulation of the vagus nerve (cranial nerve X). A generally suitable form of neurostimulator for use in the method and apparatus of the present invention is disclosed, for example, in U.S. Pat. No. 5,154,172, assigned to the same assignee as the present application. A commercially available neurostimulator system referred to as a VNS Therapy™ Pulse Generator is available from Cyberonics, Inc., Houston, Tex., the assignee of the present application. Certain parameters of the electrical signal generated by the neurostimulator are programmable, such as by means of an external programmer in a manner conventional for implantable electrical medical devices.

Embodiments of the present invention provide for an electrical stimulation of a portion of an autonomic nerve to treat a reproductive endocrine disorder. A portion of a cranial nerve (e.g., a vagus nerve) may be stimulated to affect reproductive endocrine disorders. Stimulation of a portion of the vagus nerve may be used to modify various reproductive endocrine disorders. The vagus nerve is a parasympathetic nerve. In other embodiments of the invention, an electrical signal may be applied to a sympathetic nerve, or both a parasympathetic and a sympathetic nerve. Additionally, the electrical signal may be sued as to induce afferent, efferent or afferent-efferent combination action potentials in the target nerve(s) to treat reproductive endocrine disorders. The electrical signal may also be such as to block electrical activity on the nerve. In still other embodiments, the electrical signal may comprise a plurality of signals, some of which block electrical activity on the nerve and some of which induce afferent and/or efferent action potentials on the nerve, in order to treat reproductive endocrine disorders.

In one embodiment, the present invention may comprise a medical system comprising an electrical pulse generator or stimulator to provide an electrical signal to treat a reproductive endocrine disorder. Systems of the present invention may comprise an implantable pulse generator coupled to an implanted electrode, an external pulse generator coupled to external electrodes placed on the skin of the patient to transcutaneously stimulate a cranial nerve, or partially implantable system in which the electrical pulse generator is external to the patient's body and is coupled via RF or wireless link to an implanted electrode coupled to the cranial nerve.

Turning now to FIG. 1, an implantable medical device (IMD) 100 is provided for stimulating a nerve, such as an autonomic nerve 105, to treat a reproductive endocrine disorder using neurostimulation, according to one illustrative embodiment of the present invention. The term "autonomic nerve" refers to any portion of the main trunk or any branch of a sympathetic or parasympathetic nerve, including specifically one or more cranial nerves including cranial nerve fibers, a left cranial nerve and a right cranial nerve, or any portion of the nervous system that is related to regulating the viscera of the human body. The IMD 100 may deliver an electrical signal 115 to a vagus nerve 120 (a particular embodiment of the autonomic nerve 105) that travels to the brain 125 of a patient. The vagus nerve 120 provides an electrical signal 115 to an area of the brain 125 that directly or indirectly affects or regulates the reproductive endocrine system of a patient. More generally, autonomic nerve 105 may be a nerve branch that is associated with the parasympathetic control or the sympathetic control of a reproductive endocrine function.

The IMD 100 may apply neurostimulation by delivering the electrical signal 115 to the vagus nerve 120 via a lead 135 coupled to one or more electrodes 140 (1-n). For example, the IMD 100 may stimulate an autonomic nerve 105 by applying the electrical signal 115 to the vagus nerve 120, e.g., to the main trunk of the right or left vagi, using the electrode(s) 140(1-n). The IMD 100 may also stimulate a portion of the brain 125 directly innervated by the autonomic nerve 105 or indirectly innervated by the autonomic nerve 105. Such portions of the brain may include the hypothalamus, among others.

Consistent with one embodiment of the present invention, the IMD 100 may be a neurostimulator device capable of treating a disease, disorder or condition relating to the reproductive endocrine functions of a patient by providing electrical neurostimulation therapy to a patient. In order to accomplish this task, the IMD 100 may be implanted in the patient at a suitable location. The IMD 100 may apply the electrical signal 115, which may comprise a pulsed electrical signal, to the autonomic nerve 105. The IMD 100 may generate the electrical signal 115 defined by one or more characteristics. These characteristics may be compared to one or more corresponding values within a predetermined range. The IMD 100 may apply the electrical signal 115 to a vagus nerve 120 or a nerve fascicle within the autonomic nerve 105. By applying the electrical signal 115 to an autonomic nerve 105 such as a vagus nerve 120, the IMD 100 may treat a reproductive endocrine disorder in a patient.

Implantable medical devices 100 that may be used in the present invention include any of a variety of electrical stimulation devices, such as a neurostimulator capable of stimulating a neural structure in a patient, especially for stimulating a patient's autonomic nerve, such as a vagus nerve 120. The IMD 100 is capable of delivering a controlled current stimulation signal. Although the IMD 100 is described in terms of autonomic nerve stimulation, and particularly vagus nerve stimulation, a person of ordinary skill in the art would recognize that the present invention is not so limited. For example, the IMD 100 may be applied to the stimulation of other autonomic nerves, sympathetic or parasympathetic, afferent or efferent, or other neural tissue, such as one or more brain structures of the patient.

In the generally accepted clinical labeling of cranial nerves, the tenth cranial nerve is the vagus nerve, which originates from the brainstem of the brain 125. The left and right vagus nerves emerge from the corresponding side of the brainstem. The vagus nerves pass through the foramina of the skull to parts of the head, neck and trunk. Left and right vagus nerves include both sensory and motor nerve fibers. The cell bodies of vagal sensory nerve fibers are located outside the brain 125 in ganglia groups, and the cell bodies of vagal motor nerve fibers are attached to neurons 142 located within the brain 125. The vagus nerve is a parasympathetic nerve, part of the peripheral nervous system (PNS). Somatic nerve fibers of the cranial nerves are involved in conscious activities and connect the CNS to the skin and skeletal muscles. Autonomic nerve fibers of these nerves are involved in unconscious activities and connect the CNS to the visceral organs such as the heart, lungs, stomach, liver, pancreas, spleen, and intestines. Accordingly, to provide vagus nerve stimulation, an electrical signal may be applied to the patient's vagus nerve unilaterally or bilaterally, i.e., to one or both of the left or right vagus nerve. For example, coupling the electrodes 140(1-n) comprises coupling an electrode to at least one cranial nerve selected from the group consisting of the left vagus nerve and the right vagus nerve. The term "coupling" may include actual fixation, proximate location, and the like. The electrodes 140(1-n) may be coupled to a branch of the vagus nerve of the patient. The vagus nerve 120 may be selected from the group consisting of the main trunk of the right or left vagus nerve.

Applying the electrical signal 115 to a selected autonomic nerve 105 may comprise generating a response selected from the group consisting of an afferent action potential, an efferent action potential, an afferent hyperpolarization, an efferent hyperpolarization, an afferent sub-threshold depolarization, and an efferent sub-threshold depolarization. The IMD 100 may generate an efferent action potential for treating a reproductive endocrine disorder.

The IMD 100 may comprise an electrical signal generator 150 and a controller 155 operatively coupled thereto to generate the electrical signal 115 for causing the nerve stimulation. The stimulus generator 150 may generate the electrical signal 115. The controller 155 may be adapted to apply the electrical signal 115 to the autonomic nerve 105 to provide electrical neurostimulation therapy to the patient for treating a reproductive endocrine disorder. The controller 155 may direct the stimulus generator 150 to generate the electrical signal 115 to stimulate the vagus nerve 120.

To generate the electrical signal 115, the IMD 100 may further include a power supply, such as a battery 160, a memory 165, and a communication interface 170. More specifically, the battery 160 may comprise a power-source battery that may be rechargeable. The battery 160 provides power for the operation of the IMD 100, including electronic operations and the stimulation function. The battery 160, in one embodiment, may be a lithium/thionyl chloride cell or, in another embodiment, a lithium/carbon monofluoride cell. The memory 165, in one embodiment, is capable of storing various data, such as operation parameter data, status data, and the like, as well as program code. The communication interface 170 is capable of providing transmission and reception of electronic signals to and from an external unit, for example, by telemetry or wireless telecommunication. The external unit may be a device that is capable of programming the IMD 100.

The IMD 100, which may be a single device or a plurality of devices, is implanted and electrically coupled to the lead(s) 135, which are in turn coupled to the electrode(s) 140 implanted on the left or right vagus nerve, for example. In one embodiment, the electrode(s) 140 (1-n) may include a set of stimulating electrode(s) (i.e., electrodes to deliver the electrical signal to the nerve) separate from a set of sensing electrode(s). In another embodiment, the same electrode may be deployed to stimulate and to sense. A particular type or a combination of electrodes may be selected as desired for a given application. For example, an electrode suitable for coupling to a vagus nerve 120 may be used. The electrodes 140 may comprise a bipolar stimulating electrode pair. Those skilled in the art having the benefit of the present invention will appreciate that many electrode designs could be used in the present invention.

Using the electrode(s) 140(1-n), the stimulus generator 150 may apply a predetermined electrical signal 115 to the selected autonomic nerve 105 to provide therapeutic neurostimulation for the patient with a reproductive endocrine disorder. Where the selected autonomic nerve 105 comprises the vagus nerve, the electrode(s) 140(1-n) may comprise at least one nerve electrode for implantation on the patient's vagus nerve for direct stimulation thereof. Alternatively, a nerve electrode may be implanted on or placed proximate to a branch of the patient's vagus nerve for direct stimulation thereof.

A particular embodiment of the IMD 100 may be a programmable electrical signal generator. Such a programmable electrical signal generator may be capable of programmably defining the electrical signal 115. By providing an electrical signal 115 defined by at least one parameter selected from the group consisting of a current magnitude, a pulse frequency, and a pulse width, the IMD 100 may treat a reproductive endocrine disorder. The IMD 100 may detect a symptom of the reproductive endocrine disorder. In response to detecting the symptom, the IMD 100 may initiate applying the electrical signal 115 to the nerve 105. For example, a sensor may be used to detect the symptom of a reproductive endocrine disorder. To treat the reproductive endocrine disorder, the IMD 100 may apply the electrical signal 115 during a first treatment period and further apply a second electrical signal to the autonomic nerve 105 using the electrode 140 during a second treatment period.

In one embodiment, the method may further include detecting a symptom of the reproductive endocrine disorder, wherein the applying the electrical signal 115 to the autonomic nerve 105 is initiated in response to the detecting of the symptom. In a further embodiment, the detecting the symptom may be performed by the patient. This may involve a subjective observation that the patient is experiencing a symptom of the reproductive endocrine disorder or is in or entering a portion of his/her reproductive hormone cycle wherein symptoms of the reproductive endocrine disorder are frequent, severe, or both. For example, in one embodiment, a female patient may observe the onset of menses. Alternatively, or in addition, the symptom may be detected by performing a reproductive endocrine disorder test on the patient. Physiological responses can be detected by measuring hormonal levels in bodily fluids, such as by extracting a blood sample from the patient, performing diagnostic test(s) thereon, and programming the IMD 100 in light of the results of the test(s); or using an implantable sensor to perform diagnostic test(s) on blood in vivo and programming the IMD 100 in light of the results of the test(s); among other techniques. Sensors can be implanted internally or may be located externally on the skin of the patient.

The method may be performed under a single treatment regimen or under multiple treatment regimens. "Treatment regimen" herein may refer to a parameter of the electrical signal 115, duration for applying the signal, or a duty cycle of the signal, among others. In one embodiment, applying the electrical signal 115 to the autonomic nerve 105 is performed during a first treatment period, and may further include the step of applying a second electrical signal to the cranial nerve using the electrode 140 during a second treatment period. In a further embodiment, the method may include detecting a symptom of the reproductive endocrine disorder, wherein the second treatment period is initiated upon the detection of the symptom. The patient may benefit by receiving a first electrical signal during a first, acute treatment period and a second electrical signal during a second, chronic treatment period. Three or more treatment periods may be used, if deemed desirable by a medical practitioner. In an alternative embodiment, a plurality of different electrical signals, each having at least one parameter defining the signal that is different from the other signals, may be applied to the nerve during a single treatment period. This may include alternating between two, three, or more electrical signals.

In one embodiment, one or more treatment regimens may be used in synchrony with an endogenous endocrine cycle of the patient.

Figure 2:
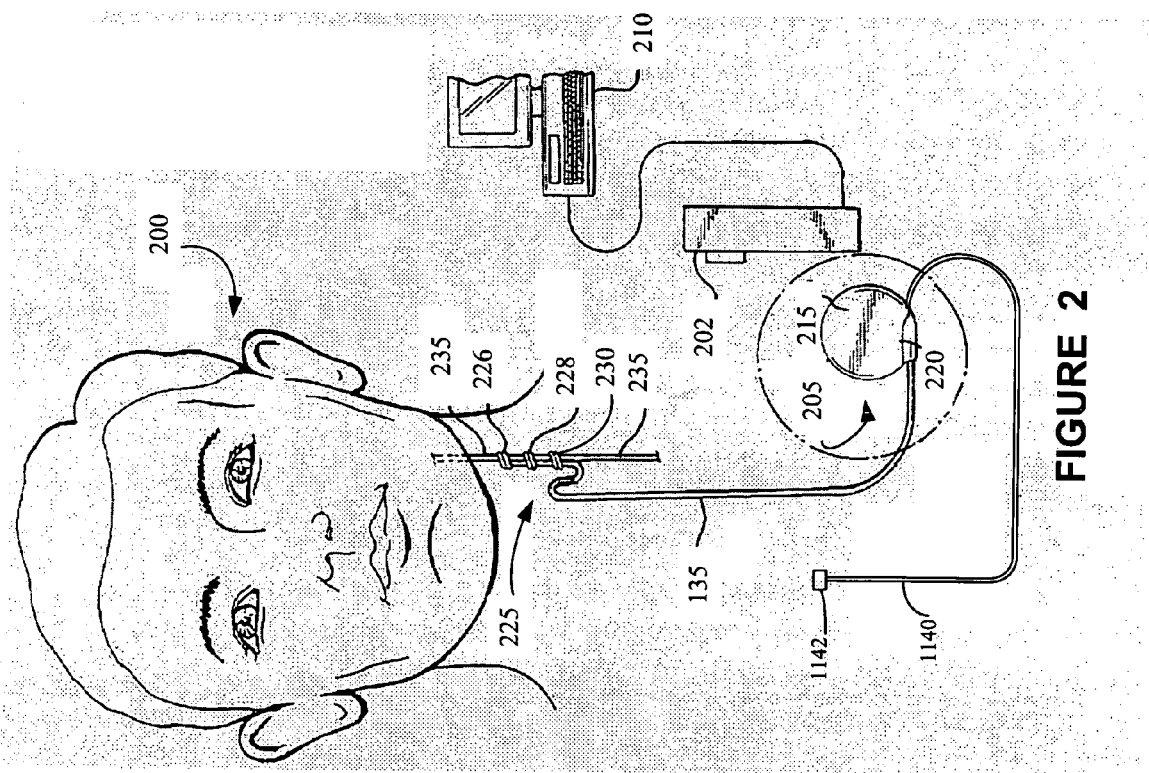
FIG. 2 illustrates one embodiment of a neurostimulator implanted into a patient's body for stimulating the vagus nerve of the patient, with an external programming user interface, in accordance with an illustrative embodiment of the present invention.

Turning now to FIG. 2, a particular embodiment of the IMD 100 shown in FIG. 1, in accordance with one illustrative embodiment of the present invention is provided. As shown therein, an electrode assembly 225, which may comprise a plurality of electrodes such as electrodes 226, 228, may be coupled to the vagus nerve 235 in accordance with an illustrative embodiment of the present invention. The lead 135 is coupled to the electrode assembly 225 and secured, while retaining the ability to flex with movement of the chest and neck. The lead 135 may be secured by a suture connection to nearby tissue. The electrode assembly 225 may deliver the electrical signal 115 to the autonomic nerve 105 to cause desired nerve stimulation for treating a reproductive endocrine disorder. Using the electrode(s) 226, 228, the selected cranial nerve such as vagus nerve 235, may be stimulated within a patient's body 200.

Although FIG. 2 illustrates a system for stimulating the left vagus nerve 235 in the neck (cervical) area, those skilled in the art having the benefit of the present disclosure will understand the electrical signal 115 for nerve stimulation may be applied to the right cervical vagus nerve in addition to, or instead of, the left vagus nerve, or to other locations of the left or right vagi, including near-diaphragmatic or sub-diaphragmatic locations of the left or right vagus nerves. More generally, the electrical signal 115 may be applied to any autonomic nerve 105 and remain within the scope of the present invention. In one embodiment, lead 135 and electrode 225 assemblies substantially as discussed above may be coupled to the same or a different electrical signal generator.

An external programming user interface 202 may be used by a health care professional or caregiver for a particular patient to either initially program or to later reprogram the IMD 100, such as a neurostimulator 205. The neurostimulator 205 may include the electrical signal generator 150, which may be programmable. To enable physician-programming of the electrical and timing parameters of a sequence of electrical impulses, an external programming system 210 may include a processor-based computing device, such as a computer, personal digital assistant (PDA) device, or other suitable computing device.

Using the external programming user interface 202, a user of the external programming system 210 may program the neurostimulator 205. Communications between the neurostimulator 205 and the external programming system 210 may be accomplished using any of a variety of conventional techniques known in the art. The neurostimulator 205 may include a transceiver (such as a coil) that permits signals to be communicated wirelessly between the external programming user interface 202, such as a wand, and the neurostimulator 205.

The neurostimulator 205 having a case 215 with an electrically conducting connector on header 220 may be implanted in the patient's chest in a pocket or cavity formed by the implanting surgeon just below the skin, much as a pacemaker pulse generator would be implanted, for example. A stimulating nerve electrode assembly 225, preferably comprising an electrode pair, is conductively connected to the distal end of an insulated electrically conductive lead assembly 135, which preferably comprises a pair of lead wires and is attached at its proximal end to the connector on the case 215. The electrode assembly 225 is surgically coupled to a vagus nerve 235 in the patient's neck. The electrode assembly 225 preferably comprises a bipolar stimulating electrode pair 226, 228, such as the electrode pair described in U.S. Pat. No. 4,573,481 issued Mar. 4, 1986 to Bullara, which is hereby incorporated by reference herein in its entirety. One exemplary electrode assembly is available from Cyberonics, Inc., Houston, Tex. as the model 302 electrode assembly. Persons of skill in the art will appreciate that many electrode designs could be used in the present invention. The two electrodes 226, 228 are preferably wrapped about the vagus nerve, and the electrode assembly 225 secured to the nerve 235 by a spiral anchoring tether 230 such as that disclosed in U.S. Pat. No. 4,979,511 issued Dec. 25, 1990 to Reese S. Terry, Jr. and assigned to the same assignee as the instant application.

In one embodiment, the open helical design of the electrode assembly 225 (described in detail in the above-cited Bullara patent), which is self-sizing and flexible, minimizes mechanical trauma to the nerve and allows body fluid interchange with the nerve. The electrode assembly 225 conforms to the shape of the nerve, providing a low stimulation threshold by allowing a large stimulation contact area. Structurally, the electrode assembly 225 comprises two electrode ribbons (not shown), of a conductive material such as platinum, iridium, platinum-iridium alloys, or oxides of the foregoing. The electrode ribbons are individually bonded to an inside surface of an elastomeric body portion of two spiral electrodes, which may comprise two spiral loops of a three-loop helical assembly.

In one embodiment, the lead assembly 230 may comprise two distinct lead wires or a coaxial cable whose two conductive elements are respectively coupled to one of the conductive electrode ribbons. One suitable method of coupling the lead wires or cable to the electrodes comprises a spacer assembly such as that depicted in U.S. Pat. No. 5,531,778 issued Jul. 2, 1996, to Steven Maschino, et al. and assigned to the same Assignee as the instant application, although other known coupling techniques may be used. The elastomeric body portion of each loop is preferably composed of silicone rubber, and the third loop acts as the anchoring tether for the electrode assembly 225.

In one embodiment, the electrode(s) 140 (1-n) of IMD 100 (FIG. 1) may sense or detect any target symptom parameter in the patient's body 200. For example, an electrode 140 coupled to the patient's vagus nerve may detect a factor associated with a reproductive endocrine disorder. The electrode(s) 140 (1-n) may sense or detect a reproductive endocrine disorder condition. For example, a sensor or any other element capable of providing a sensing signal representative of a patient's body parameter associated with activity of the reproductive endocrine functions may be deployed. In another embodiment, the IMD 100 can comprise a dedicated sensor, such as sensor 1142 (FIG. 2).

The electrode(s) 140(1-n), as shown in FIG. 1 may be used in some embodiments of the invention to trigger administration of the electrical stimulation therapy to the vagus nerve 235 via electrode assembly 225. Use of such sensed body signals to trigger or initiate stimulation therapy is hereinafter referred to as "active," "triggered," or "feedback" modes of administration. Other embodiments of the present invention utilize a continuous, periodic or intermittent stimulus signal. These signals may be applied to the vagus nerve (each of which constitutes a form of continual application of the signal) according to a programmed on/off duty cycle. Sensors need not be used to trigger therapy delivery. This type of delivery may be referred to as a "passive" or "prophylactic" therapy mode. Both active and passive electrical biasing signals may be combined or delivered by a single neurostimulator according to the present invention.

The electrical signal generator 150 may be programmed using programming software of the type copyrighted by the assignee of the instant application with the Register of Copyrights, Library of Congress, or other suitable software based on the description herein. A programming wand (not shown) may be used to facilitate radio frequency (RF) communication between the external programming user interface 202 and the electrical signal generator 150. The wand and software permit noninvasive communication with the electrical signal generator 150 after the neurostimulator 205 is implanted. The wand may be powered by internal batteries, and provided with a "power on" light to indicate sufficient power for communication. Another indicator light may be provided to show that data transmission is occurring between the wand and the neurostimulator 205.

The neurostimulator 205 may provide vagus nerve stimulation therapy upon a vagus nerve 235 or to any portion of the autonomic nervous system. The neurostimulator 205 may be activated manually or automatically to deliver the electrical bias signal to the selected cranial nerve via the electrode(s) 226, 228. The neurostimulator 205 may be programmed to deliver the electrical signal 115 continuously, periodically or intermittently when activated.

The "operatively coupled" feature may include actual contact of the electrode to portions of the nerves described above. The term "operatively coupled" may also include sufficient proximity of the placement of the electrodes to the nerve portions, such that an electrical signal sent to the electrode is capable of stimulating various portions of the vagus nerve described herein.

In one embodiment, electrical signal 115 may be applied so as to generate efferent action potentials, i.e., signals traveling on a nerve in a direction away from the central nervous system. Thus, the electrical signal 115 may be employed using the IMD 100, such that afferent fibers are not stimulated, or efferent fibers are stimulated. Additionally, the electrical signal 115 may be applied to provide a "blocking" of action potentials traveling along the nerve 105. By providing an electrical signal for efferent stimulation or for blocking, an appreciable interruption of afferent signals sent to the brain via the vagus nerve may be achieved.

Further, the electrical signal 115 may be applied so as to induce afferent action potentials in an autonomic nerve 105. This may be done while also inducing efferent action potentials, or while blocking efferent action potentials on the nerve. Various reproductive endocrine disorders may be treated by performing afferent stimulation of the vagus nerve. Efferent blocking may be realized by enhancing the hyperpolarization of a stimulation signal, as described below. Embodiments of the present invention may employ the IMD 100 to perform stimulation in combination with signal blocking, in order to treat reproductive endocrine disorders. Using the stimulation from the IMD 100, parasympathetic nerve portions may be inhibited such that blocking of stimulation is achieved, wherein the various portions of the parasympathetic nerve may also be stimulated so as to induce afferent and/or efferent action potentials on the nerve and thereby affect a reproductive endocrine mechanism in the patients' body. In this way, afferent and/or efferent stimulation may be performed by the IMD 100 to treat various reproductive endocrine disorders.

The electrical stimulation treatment described herein may be used to treat reproductive endocrine disorders separately, or in combination with another type of treatment. For example, electrical stimulation treatment may be applied in combination with a chemical agent, such as various drugs, to treat various disorders relating to the reproductive endocrine system. Therefore, various drugs may be taken by a patient, wherein the effects of these drugs may be enhanced by additionally providing electrical stimulation to various portions of the nerves described herein to treat reproductive endocrine disorders. Accordingly, systems of the present invention may comprise a drug delivery device to deliver one or more of follicle stimulating hormone (FSH), luteinizing hormone (LH), human chorionic gonadotropin (hCG), a luteinizing hormone-releasing hormone (LHRH) agonist, an estrogen, an anti-androgen, selective estrogen reuptake modulators, hormone replacement therapy drug, oxytocin, and a steroid. Further, the electrical stimulation may be performed in combination with treatment(s) relating to a biological agent, such as hormones. Therefore, hormone therapy may be enhanced by the application of the stimulation provided by the IMD 100. The electrical stimulation treatment may also be performed in combination with other types of treatment, such as magnetic stimulation treatment or biological treatments. Combining the electrical stimulation with the chemical, magnetic, or biological treatments, side effects associated with certain drugs or biological agents may be reduced.

Figure 3A:
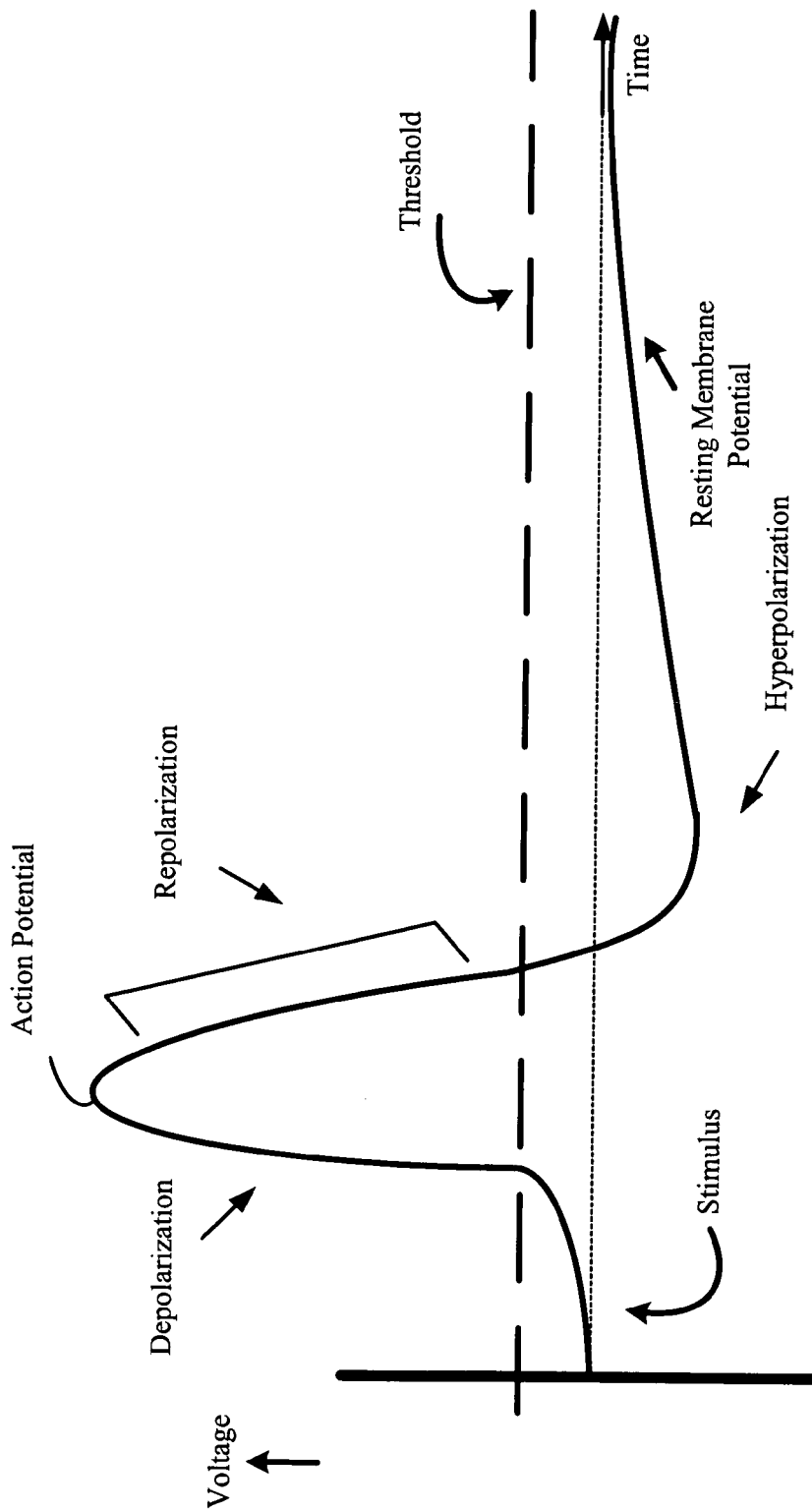
FIG. 3A illustrates an exemplary electrical signal of a firing neuron as a graph of voltage at a given location at particular times during firing by the neurostimulator of FIG. 2, when applying an electrical signal to the autonomic nerves, in accordance with one illustrative embodiment of the present invention.

FIG. 3A provides a stylized depiction of an exemplary electrical signal of a firing neuron as a graph of voltage at a given location at particular times during firing, in accordance with one embodiment of the present invention. A typical neuron has a resting membrane potential of about −70 mV, maintained by transmembrane ion channel proteins. When a portion of the neuron reaches a firing threshold of about −55 mV, the ion channel proteins in the locality allow the rapid ingress of extracellular sodium ions, which depolarizes the membrane to about +30 mV. The wave of depolarization then propagates along the neuron. After depolarization at a given location, potassium ion channels open to allow intracellular potassium ions to exit the cell, lowering the membrane potential to about −80 mV (hyperpolarization). About 1 msec is required for transmembrane proteins to return sodium and potassium ions to their starting intra- and extracellular concentrations and allow a subsequent action potential to occur. The present invention may raise or lower the resting membrane potential, thus making the reaching of the firing threshold more or less likely and subsequently increasing or decreasing the rate of fire of any particular neuron.

Referring to FIG. 3B, an exemplary electrical signal response is illustrated of a firing neuron as a graph of voltage at a given location at particular times during firing by the neurostimulator of FIG. 2, in accordance with one illustrative embodiment of the present invention. As shown in FIG. 3C, an exemplary stimulus including a sub-threshold depolarizing pulse and additional stimulus to the cranial nerve 105, such as the vagus nerve 235, may be applied for firing a neuron, in accordance with one illustrative embodiment of the present invention. The stimulus illustrated in FIG. 3C depicts a graph of voltage at a given location at particular times by the neurostimulator of FIG. 2.

The neurostimulator may apply the stimulus voltage of FIG. 3C to the autonomic nerve 105, which may include afferent fibers, efferent fibers, or both. This stimulus voltage may cause the response voltage shown in FIG. 3B. Afferent fibers transmit information to the brain from the extremities; efferent fibers transmit information from the brain to the extremities. The vagus nerve 235 may include both afferent and efferent fibers, and the neurostimulator 205 may be used to stimulate either or both.

The autonomic nerve 105 may include fibers that transmit information in the sympathetic nervous system, the parasympathetic nervous system, or both. Inducing an action potential in the sympathetic nervous system may yield a result similar to that produced by blocking an action potential in the parasympathetic nervous system and vice versa.

Figures 4A, 4B:
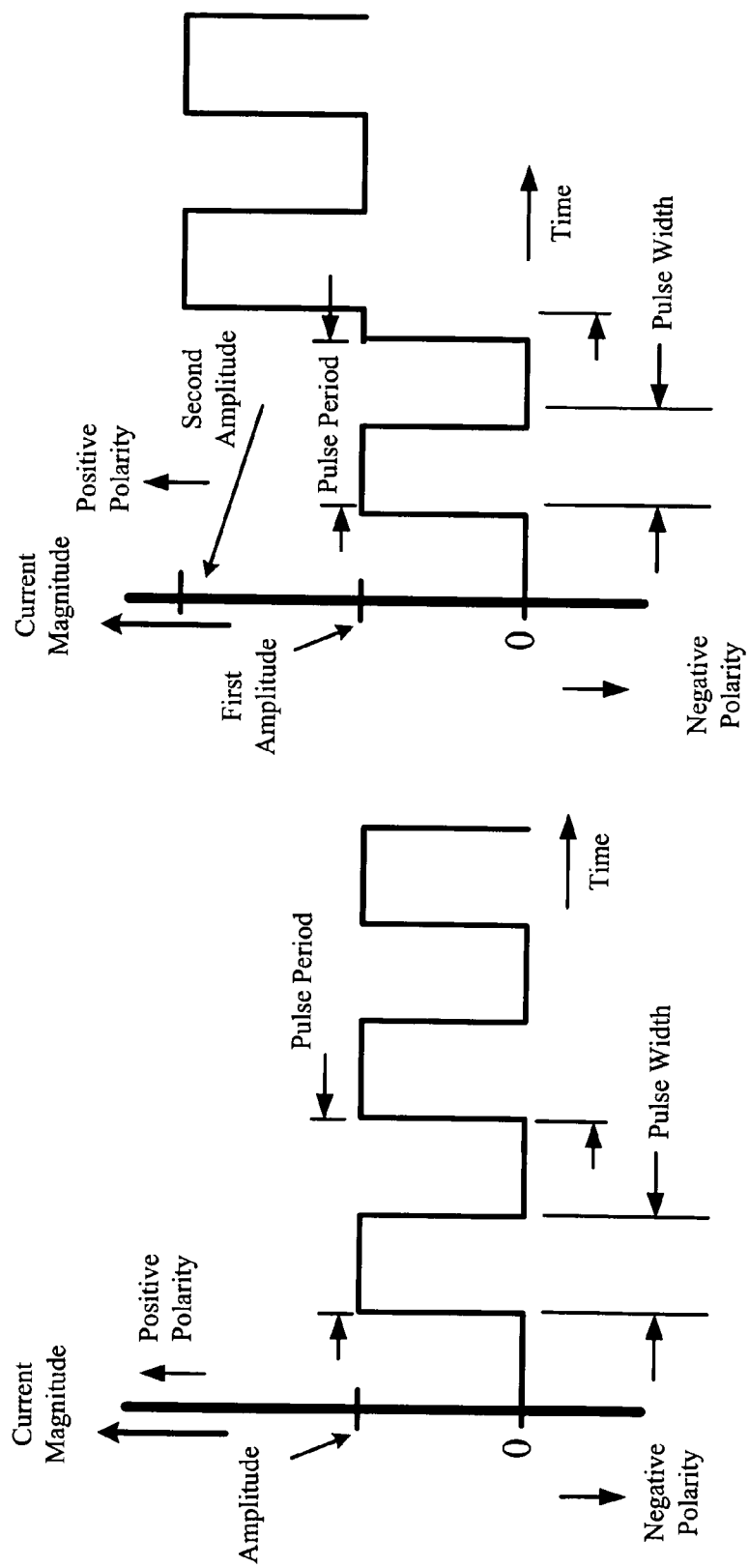
FIGS. 4A, 4B, and 4C illustrate exemplary waveforms for generating the electrical signals for stimulating the vagus nerve for treating a reproductive endocrine disorder, according to one illustrative embodiment of the present invention.
Figure 4C:
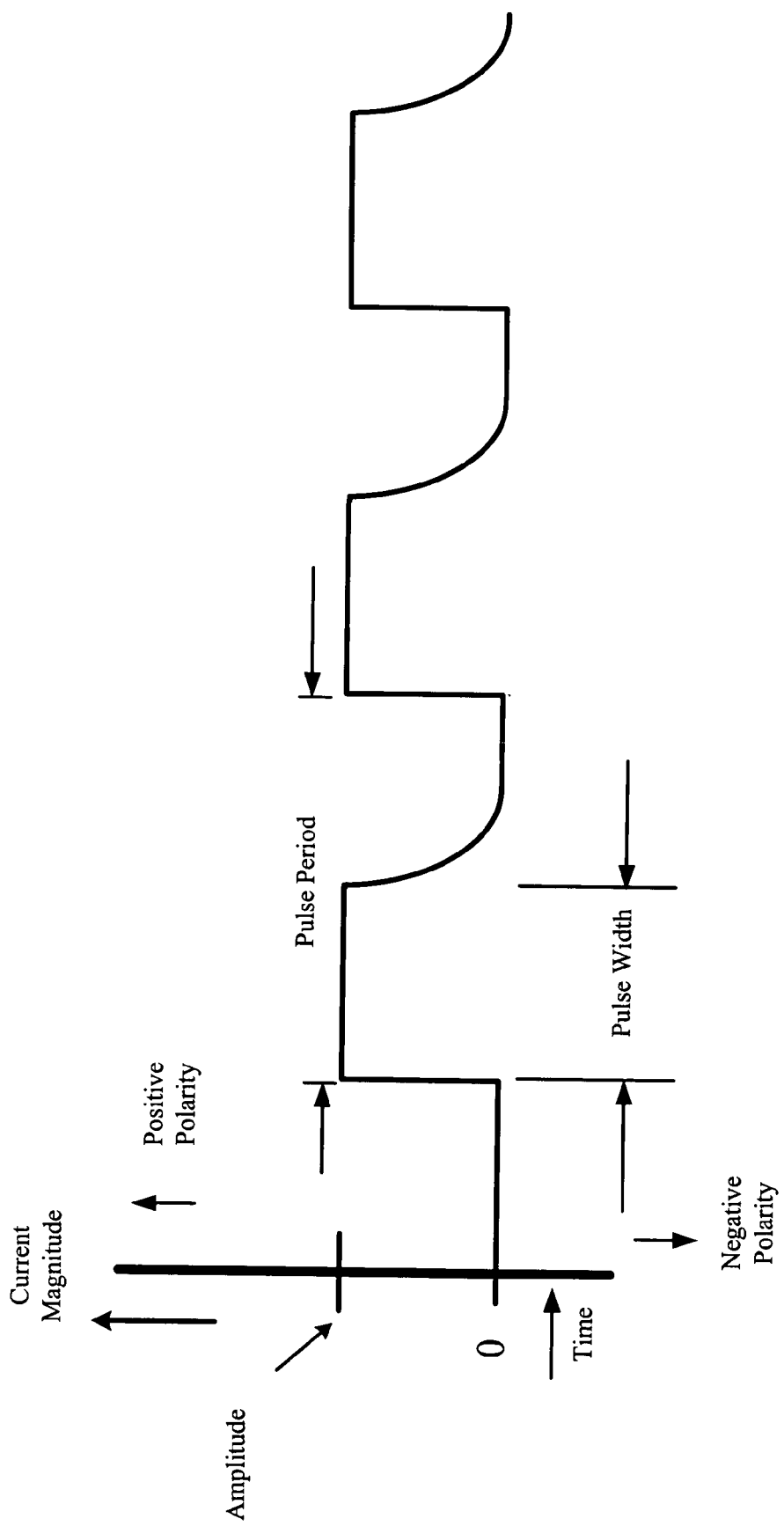

Referring back to FIG. 2, the neurostimulator 205 may generate the electrical signal 115 according to one or more programmed parameters for stimulation of the vagus nerve 235. In one embodiment, the stimulation parameter may be selected from the group consisting of a current magnitude, a pulse frequency, a pulse width, on-time, and off-time. An exemplary table of ranges for each of these stimulation parameters is provided in Table 1. The stimulation parameter may be of any suitable waveform; exemplary waveforms in accordance with one embodiment of the present invention are shown in FIGS. 4A-4C. Specifically, the exemplary waveforms illustrated in FIGS. 4A-4C depict the generation of the electrical signal 115 that may be defined by a factor related to the serum level of at least one reproductive hormone, and a condition relating to at least one of gonadal dysgenesis, hypogonadism, hypergonadism, delayed puberty, amenorrhea, infertility, premature menopause, and polycystic ovarian disease, among other reproductive endocrine disorders, relative to a value within a defined range.

According to one illustrative embodiment of the present invention, various electrical signal patterns may be employed by the neurostimulator 205. These electrical signals may include a plurality of types of pulses, e.g., pulses with varying amplitudes, polarity, frequency, etc. For example, the exemplary waveform 4A depicts that the electrical signal 115 may be defined by fixed amplitude, constant polarity, pulse width, and pulse period. The exemplary waveform 4B depicts that the electrical signal 115 may be defined by a variable amplitude, constant polarity, pulse width, and pulse period. The exemplary waveform 4C depicts that the electrical signal 115 may be defined by a fixed amplitude pulse with a relatively slowly discharging current magnitude, constant polarity, pulse width, and pulse period. Other types of signals may also be used, such as sinusoidal waveforms, etc. The electrical signal may be controlled current signals.

TABLE 1

| PARAMETER | RANGE |
| --- | --- |
| Output current | 0.1-6.0 mA |
| Pulse width | 10-1500 μsec |
| Frequency | 0.5-2500 Hz |
| On-time | 1 sec and greater |
| Off-time | 0 sec and greater |
| Frequency Sweep | 10-100 Hz |
| Random Frequency | 10-100 Hz |

On-time and off-time parameters may be used to define an intermittent pattern in which a repeating series of signals may be generated for stimulating the nerve 105 during the on-time.

Such a sequence may be referred to as a "pulse burst." This sequence may be followed by a period in which no signals are generated. During this period, the nerve is allowed to recover from the stimulation during the pulse burst. The on/off duty cycle of these alternating periods of stimulation and idle periods may have a ratio in which the off-time may be set to zero, providing continuous stimulation. Alternatively, the idle time may be as long as one day or more, in which case the stimulation is provided once per day or at even longer intervals. Typically, however, the ratio of "off-time" to "on-time" may range from about 0.5 to about 10 min.

In one embodiment, the width of each signal may be set to a value not greater than about 1 msec, such as about 250-500 μsec, and the signal repetition frequency may be programmed to be in a range of about 20-2500 Hz. A non-uniform frequency may also be used. Frequency may be altered during a pulse burst by either a frequency sweep from a low frequency to a high frequency, or vice versa. Alternatively, the timing between adjacent individual signals within a burst may be randomly changed such that two adjacent signals may be generated at any frequency within a range of frequencies.

In one embodiment, the present invention may include coupling of at least one electrode to each of two or more cranial nerves. (In this context, two or more cranial nerves mean two or more nerves having different names or numerical designations, and do not refer to the left and right versions of a particular nerve). In one embodiment, at least one electrode 140 may be coupled to each of the vagus nerve 235 or a branch of the vagus nerve. The electrode 140 may be operatively coupled to the main trunk of the right vagus nerve or the main trunk of the left vagus nerve. The term "operatively" coupled may include directly or indirectly coupling. Each of the nerves in this embodiment or others involving two or more cranial nerves may be stimulated according to particular activation modalities that may be independent between the two nerves.

Another activation modality for stimulation is to program the output of the neurostimulator 205 to the maximum amplitude which the patient may tolerate. The stimulation may be cycled on and off for a predetermined period of time followed by a relatively long interval without stimulation. Where the cranial nerve stimulation system is completely external to the patient's body, higher current amplitudes may be needed to overcome the attenuation resulting from the absence of direct contact with the vagus nerve 235 and the additional impedance of the skin of the patient. Although external systems typically require greater power consumption than implantable ones, they have an advantage in that their batteries may be replaced without surgery.

Other types of indirect stimulations may be performed in conjunction with embodiments of the invention. In one embodiment, the invention includes providing noninvasive transcranial magnetic stimulation (TMS) to the brain 125 of the patient along with the IMD 100 of the present information to treat the reproductive endocrine disorder. TMS systems include those disclosed in U.S. Pat. Nos. 5,769,778; 6,132, 361; and 6,425,852. Where TMS is used, it may be used in conjunction with cranial nerve stimulation as an adjunctive therapy. In one embodiment, both TMS and direct cranial nerve stimulation may be performed to treat the reproductive endocrine disorder. Other types of stimulation, such as chemical stimulation to treat reproductive endocrine disorders may be performed in combination with the IMD 100.

Returning to systems for providing autonomic nerve stimulation, such as that shown in FIGS. 1 and 2, stimulation may be provided in at least two different modalities. Where cranial nerve stimulation is provided based solely on pro- grammed off-times and on-times, the stimulation may be referred to as passive, inactive, or non-feedback stimulation. In contrast, stimulation may be triggered by one or more feedback loops according to changes in the body or mind of the patient. This stimulation may be referred to as active or feedback-loop stimulation. In one embodiment, feedback-loop stimulation may be manually-triggered stimulation, in which the patient manually causes the activation of a pulse burst outside of the programmed on-time/off-time cycle. The patient may manually activate the neurostimulator 205 to stimulate the autonomic nerve 105 to treat an acute episode of a reproductive endocrine disorder, such as may occur at a specific time in one of his/her reproductive endocrine cycles. The patient may also be permitted to alter the intensity of the signals applied to the autonomic nerve within limits established by the physician. For example, the patient may be permitted to alter the signal frequency, current, duty cycle, or a combination thereof. In at least some embodiments, the neurostimulator 205 may be programmed to generate the stimulus for a relatively long period of time in response to manual activation.

Patient activation of a neurostimulator 205 may involve use of an external control magnet for operating a reed switch in an implanted device, for example. Certain other techniques of manual and automatic activation of implantable medical devices are disclosed in U.S. Pat. No. 5,304,206 to Baker, Jr., et al., assigned to the same assignee as the present application ("the '206 patent"). According to the '206 patent, means for manually activating or deactivating the electrical signal generator 150 may include a sensor such as piezoelectric element mounted to the inner surface of the generator case and adapted to detect light taps by the patient on the implant site. One or more taps applied in fast sequence to the skin above the location of the electrical signal generator 150 in the patient's body 200 may be programmed into the implanted medical device 100 as a signal for activation of the electrical signal generator 150. Two taps spaced apart by a slightly longer duration of time may be programmed into the IMD 100 to indicate a desire to deactivate the electrical signal generator 150, for example. The patient may be given limited control over operation of the device to an extent which may be determined by the program dictated or entered by the attending physician. The patient may also activate the neurostimulator 205 using other suitable techniques or apparatus.

In some embodiments, feedback stimulation systems other than manually-initiated stimulation may be used in the present invention. An autonomic nerve stimulation system provided by embodiments of the present invention may include a sensing lead coupled at its proximal end to a header along with a stimulation lead and electrode assemblies. A sensor may be coupled to the distal end of the sensing lead. The sensor may include a temperature sensor, a hormone level sensor, a heart parameter sensor, a brain parameter sensor, or a sensor for another body parameter. The sensor may also include a nerve sensor for sensing activity on a nerve, such as a cranial nerve, such as the vagus nerve 235.

In one embodiment, the sensor may sense a body parameter that corresponds to a symptom of a reproductive endocrine disorder. If the sensor is to be used to detect a symptom of the reproductive endocrine disorder, a signal analysis circuit may be incorporated into the neurostimulator 205 for processing and analyzing signals from the sensor. Upon detection of the symptom of the reproductive endocrine disorder, the processed digital signal may be supplied to a microprocessor in the neurostimulator 205 to trigger application of the electrical signal 115 to the autonomic nerve 105. In another embodiment, the detection of a symptom of interest may trigger a stimulation program including different stimulation parameters from a passive stimulation program. This may entail providing a higher current stimulation signal or providing a higher ratio of on-time to off-time.

In response to the afferent action potentials, the detection communicator may detect an indication of change in the symptom characteristic. The detection communicator may provide feedback for the indication of change in the symptom characteristic to modulate the electrical signal 115. In response to providing feedback for the indication, the electrical signal generator 150 may adjust the afferent action potentials to enhance efficacy of a drug in the patient.

The neurostimulator 205 may use the memory 165 to store disorder data and a routine to analyze this data. The disorder data may include sensed body parameters or signals indicative of the sensed parameters. The routine may comprise software or firmware instructions to analyze the sensed hormonal activity for determining whether electrical neurostimulation would be desirable. If the routine determines that electrical neurostimulation is desired, then the neurostimulator 205 may provide an appropriate electrical signal to a neural structure, such as the vagus nerve 235.

In another embodiment, the sensor may detect at least one parameter indicative of at least one characteristic of at least one endogenous endocrine cycle of the patient, such as one or more of the period or the amplitude of an endocrine cycle associated with the reproductive endocrine disorder. In response to such data, the IMD 100 may modify the electrical signal in response to detecting said period or said amplitude.

In certain embodiments, the IMD 100 may comprise a neurostimulator 205 having a case 215 as a main body in which the electronics described in FIGS. 1-2 may be enclosed and hermetically sealed. Coupled to the main body may be the header 220 designed with terminal connectors for connecting to a proximal end of the electrically conductive lead(s) 135. The main body may comprise a titanium shell, and the header may comprise a clear acrylic or other hard, biocompatible polymer such as polycarbonate, or any material that may be implantable into a human body. The lead(s) 135 projecting from the electrically conductive lead assembly 230 of the header may be coupled at a distal end to electrodes 140(1-n). The electrodes 140(1-n) may be coupled to neural structure such as the vagus nerve 235, using a variety of methods for operatively coupling the lead(s) 135 to the tissue of the vagus nerve 235. Therefore, the current flow may take place from one terminal of the lead 135 to an electrode such as electrode 226 (FIG. 2) through the tissue proximal to the vagus nerve 235, to a second electrode such as electrode 228 and a second terminal of the lead 135.

Figure 5:
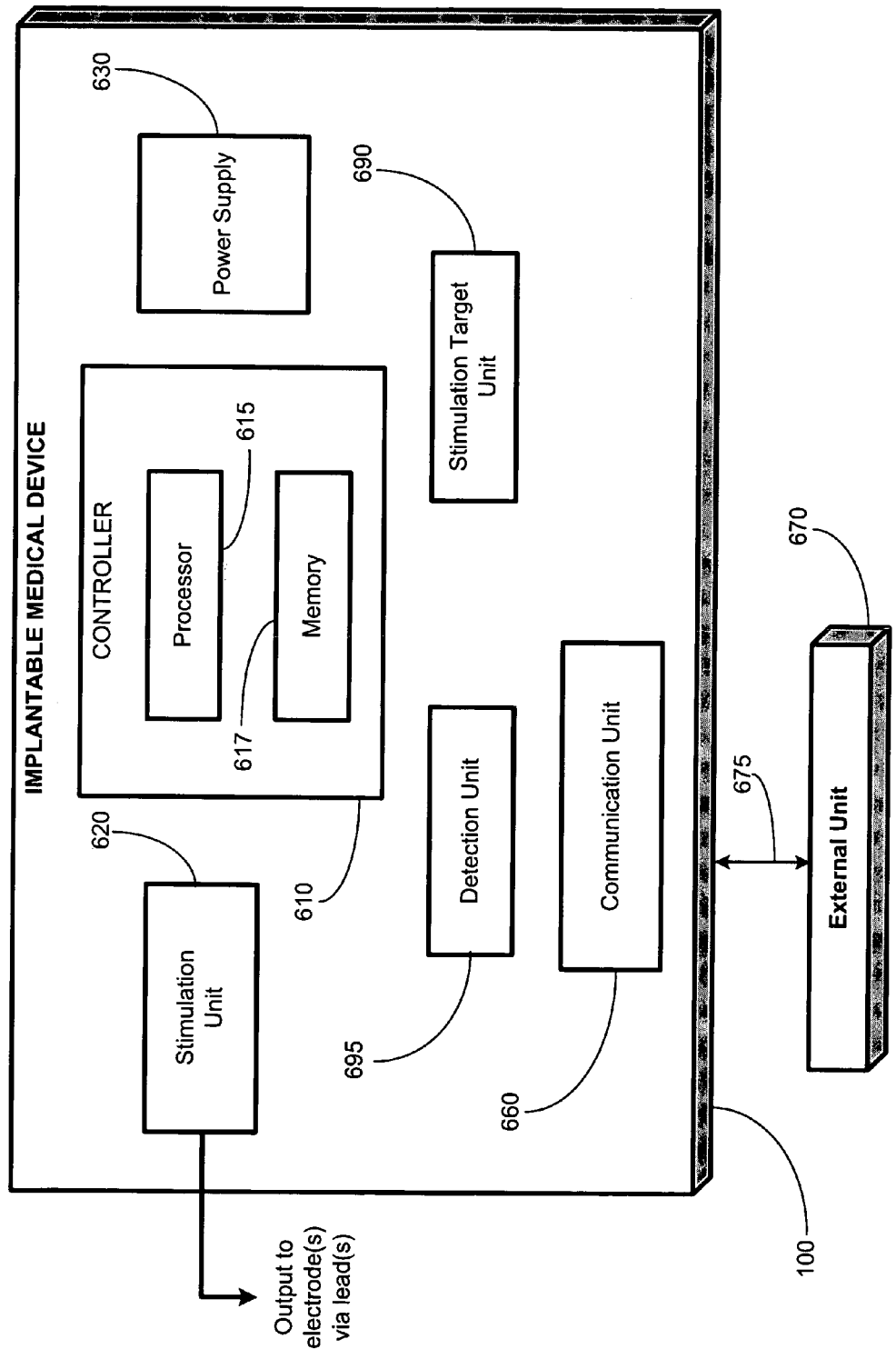
FIG. 5 illustrates a stylized block diagram depiction of the implantable medical device for treating a reproductive endocrine disorder, in accordance with one illustrative embodiment of the present invention.

Turning now to FIG. 5, a block diagram depiction of the IMD 100, in accordance with an illustrative embodiment of the present invention is provided. The IMD 100 may comprise a controller 610 capable of controlling various aspects of the operation of the IMD 100. The controller 610 is capable of receiving internal data or external data and generating and delivering a stimulation signal to target tissues of the patient's body. For example, the controller 610 may receive manual instructions from an operator externally, or may perform stimulation based on internal calculations and programming. The controller 610 is capable of affecting substantially all functions of the IMD 100.

The controller 610 may comprise various components, such as a processor 615, a memory 617, etc. The processor 615 may comprise one or more microcontrollers, microprocessors, etc., that are capable of performing various executions of software components. The memory 617 may comprise various memory portions where a number of types of data (e.g., internal data, external data instructions, software codes, status data, diagnostic data, etc.) may be stored. The memory 617 may comprise random access memory (RAM) dynamic random access memory (DRAM), electrically erasable programmable read-only memory (EEPROM), flash memory, etc.

The IMD 100 may also comprise a stimulation unit 620. The stimulation unit 620 is capable of generating and delivering stimulation signals to one or more electrodes via leads. A number of leads 122, 134, 137 may be coupled to the IMD 100. Therapy may be delivered to the leads 122 by the stimulation unit 620 based upon instructions from the controller 610. The stimulation unit 620 may comprise various circuitry, such as stimulation signal generators, impedance control circuitry to control the impedance "seen" by the leads, and other circuitry that receives instructions relating to the type of stimulation to be performed. The stimulation unit 620 is capable of delivering a controlled current stimulation signal over the leads 122.

The IMD 100 may also comprise a power supply 630. The power supply 630 may comprise a battery, voltage regulators, capacitors, etc., to provide power for the operation of the IMD 100, including delivering the stimulation signal. The power supply 630 comprises a power-source battery that in some embodiments may be rechargeable. In other embodiments, a non-rechargeable battery may be used. The power supply 630 provides power for the operation of the IMD 100, including electronic operations and the stimulation function. The power supply 630 may comprise a lithium/thionyl chloride cell or a lithium/carbon monofluoride cell. Other battery types known in the art of implantable medical devices may also be used.

The IMD 100 also comprises a communication unit 660 capable of facilitating communications between the IMD 100 and various devices. In particular, the communication unit 660 is capable of providing transmission and reception of electronic signals to and from an external unit 670. The external unit 670 may be a device that is capable of programming various modules and stimulation parameters of the IMD 100. In one embodiment, the external unit 670 is a computer system that is capable of executing a data-acquisition program. The external unit 670 may be controlled by a healthcare provider, such as a physician, at a base station in, for example, a doctor's office. The external unit 670 may be a computer, preferably a handheld computer or PDA, but may alternatively comprise any other device that is capable of electronic communications and programming. The external unit 670 may download various parameters and program software into the IMD 100 for programming the operation of the implantable device. The external unit 670 may also receive and upload various status conditions and other data from the IMD 100. The communication unit 660 may be hardware, software, firmware, or any combination thereof. Communications between the external unit 670 and the communication unit 660 may occur via a wireless or other type of communication, illustrated generally by line 675 in FIG. 5.

The IMD 100 also comprises a detection unit 695 that is capable of detecting various conditions or characteristics of the reproductive endocrine function(s) of a patient. For example, the detection unit 695 may comprise hardware, software, or firmware that are capable of determining data relating to a reproductive endocrine disorder. The detection unit 695 may comprise means for deciphering data from various sensors that are capable of measuring factors related to the reproductive endocrine disorder. Based upon the data deciphered by the detection unit 695, the IMD 100 may deliver stimulation to a portion of the autonomous nerve to affect the reproductive endocrine function(s) of the patient. In one embodiment, the detection unit 695 may be capable of detecting a feedback response from the patient. The feedback response may include a magnetic signal input, a tap input, a wireless data input to the IMD 100, etc. The feedback may be indicative of a pain and/or noxious threshold, wherein the threshold may be the limit of tolerance of discomfort for a particular patient. The pain or discomfort may relate to various symptoms of an endocrine disorder such as, without limitation, gonadal dysgenesis, hypogonadism, hypergonadism, delayed puberty, amenorrhea, infertility, premature menopause, or polycystic ovarian syndrome, osteoporosis, hirsutism, and sarcopenia.

The IMD 100 may also comprise a stimulation target unit 690 that is capable of directing a stimulation signal to one or more electrodes that is operationally coupled to various portions of the autonomic nerves. The stimulation target unit 690 may direct a stimulation signal to the left vagus main trunk, the right vagus main trunk, or a branch of the left or right vagus nerve. In this way, the stimulation target unit is capable of targeting a predetermined portion of the vagus nerve. Therefore, based upon a particular type of data detected by the detection unit 695, the stimulation target unit 690 may perform an afferent, an efferent, or an afferent-efferent combination stimulation to treat a reproductive endocrine disorder. Therefore, upon an onset of a reproductive endocrine disorder, the IMD 100 may select various portions of the autonomous nerve described herein to stimulate to perform an efferent, an afferent, or an afferent-efferent combination stimulation in order to alleviate the reproductive endocrine disorder. Further, the stimulation target unit 690 may be capable of directing the IMD 200 to deliver a sensory stimulus signal to the patient. The sensory stimulus signal may include a pain stimulus, a noxious stimulus, temperature stimulus, and/or any type of sensory stimulus.

One or more blocks illustrated in the block diagram of IMD 100 in FIG. 5 may comprise hardware units, software units, firmware units or any combination thereof. Additionally, one or more blocks illustrated in FIG. 5 may be combined with other blocks, which may represent circuit hardware units, software algorithms, etc. Additionally, any number of the circuitry or software units associated with the various blocks illustrated in FIG. 5 may be combined into a programmable device, such as a field programmable gate array, an ASIC device, etc.

Figure 6:
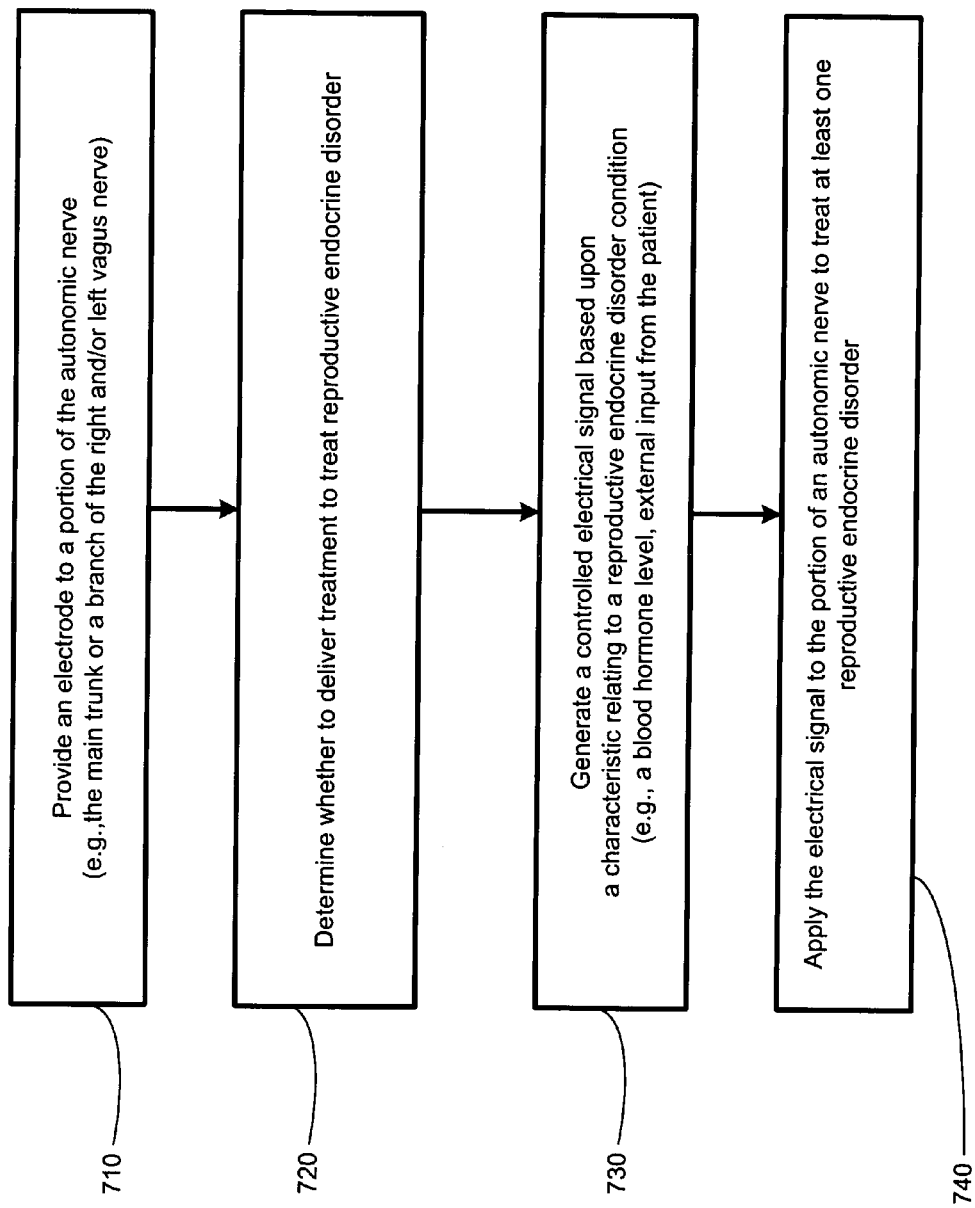
FIG. 6 illustrates a flowchart depiction of a method for treating a reproductive endocrine disorder, in accordance with illustrative embodiment of the present invention.

Turning now to FIG. 6, a flowchart depiction of a method for treating a reproductive endocrine disorder, in accordance with one illustrative embodiment of the present invention is provided. An electrode may be coupled to a portion of an autonomous nerve to perform a stimulation function or a blocking function to treat a reproductive endocrine disorder. In one embodiment, one or more electrodes may be positioned in electrical contact or proximate to a portion of the autonomic nerve to deliver a stimulation signal to the portion of the autonomic nerve (block 710). A determination may be made as to whether a treatment for motion sickness should be provided (block 720). In one embodiment, this determination may include receiving an external input (e.g., a magnetic input, a tap input, a wireless communications input, etc.) indicative of a request for treatment. In another embodiment, an automated sensing of an indication of motion sickness may be performed, prompting the determination to provide treatment. In yet another embodiment, an external input may trigger a detection algorithm to sense an indication of motion sickness, prompting a determination to provide treatment. The electrodes may be operatively coupled to at least one of main trunk of the right or left vagus nerve.

The IMD 100 may then generate a controlled electrical signal, based upon one or more characteristic relating to the reproductive endocrine disorder(s) of the patient (block 730). This may include a predetermined electrical signal that is preprogrammed based upon a particular condition of a patient. For example, a physician may pre-program the type of stimulation to provide (e.g., efferent, afferent, or afferent-efferent combination stimulation) in order to treat the patient based upon the type of reproductive endocrine disorder of the patient. The type of simulation may be based on various physical characteristics of the patient, as well as on the type and severity of the disorder. The IMD 100 may then generate a signal, such as a controlled-current pulse signal, to affect the operation of one or more portions of the reproductive endocrine system of a patient.

In another embodiment, application of the stimulation signal may be designed to promote a blocking effect relating to a signal that is being sent from the brain to the various portions of the reproductive endocrine system to treat the reproductive endocrine disorder. This may be accomplished by delivering a particular type of controlled electrical signal, such as a controlled current signal to the autonomic nerve. In yet another embodiment, afferent fibers may also be stimulated in combination with an efferent blocking to treat a reproductive endocrine disorder.

Additional functions, such as a detection process, may be alternatively employed with the embodiment of the present invention. The detection process may be employed such that an external detection or an internal detection of a bodily function may be used to adjust the operation of the IMD 100.

Figure 7:
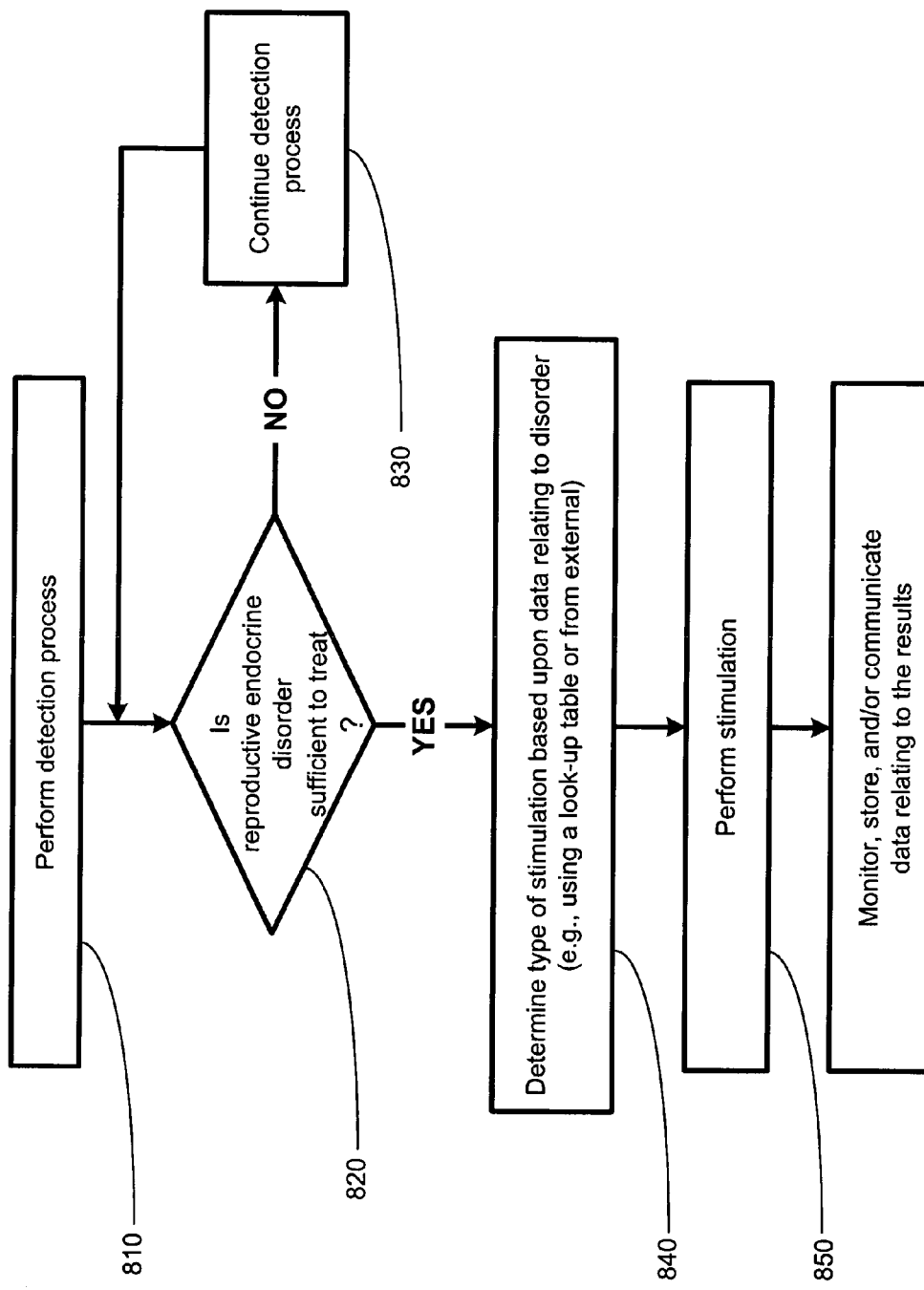
FIG. 7 illustrates a flowchart depiction of an alternative method for treating a reproductive endocrine disorder, in accordance with an alternative illustrative embodiment of the present invention.

Turning now to FIG. 7, a block diagram depiction of a method in accordance with an alternative embodiment of the present invention is illustrated. The IMD 100 may perform a database detection process (block 810). The detection process may encompass detecting a variety of types of characteristics of reproductive endocrine activity, external input from the patient, etc. A more detailed depiction of the steps for performing the detection process is provided in FIG. 8, and accompanying description below. Upon performing the detection process, the IMD 100 may determine whether a detected symptom of a reproductive endocrine disorder is sufficiently severe to treat based upon the measurements performed during the detection process (block 820). For example, a blood hormone level may be examined to determine whether it is greater than or less than a predetermined range of values where intervention by the IMD 100 is desirable. Upon a determination that the disorder is insufficient to treat by the IMD 100, the detection process is continued (block 830).

Upon a determination that the disorder is sufficient to treat using the IMD 100, a determination as to the type of stimulation based upon data relating to the disorder is made (block 840). The type of stimulation may be determined in a variety of manners, such as performing a look-up in a look-up table that may be stored in the memory 617. Alternatively, the type of stimulation may be determined by an input from an external source, such as the external unit 670 or an input from the patient. Further, determination of the type of stimulation may also include determining the location as to where the stimulation is to be delivered. Accordingly, the selection of particular electrodes, which may be used to deliver the stimulation signal, is made. A more detailed description of the determination of the type of stimulation signal is provided in FIG. 9 and accompanying description below.

Upon determining the type of stimulation to be delivered, the IMD 100 performs the stimulation by delivering the electrical signal to one or more selected electrodes (block 850).

Upon delivery of the stimulation, the IMD 100 may monitor, store, or compute the results of the stimulation (block 860). For example, based upon the calculation, a determination may be made that adjustment(s) to the type of signal to be delivered for stimulation, may be performed. Further, the calculations may reflect the need to deliver additional stimulation. Additionally, data relating to the results of stimulation may be stored in memory 617 for later extraction or further analysis. Also, in one embodiment, real time or near real time communications may be provided to communicate the stimulation result or the stimulation log to an external unit 670.

Figure 8:
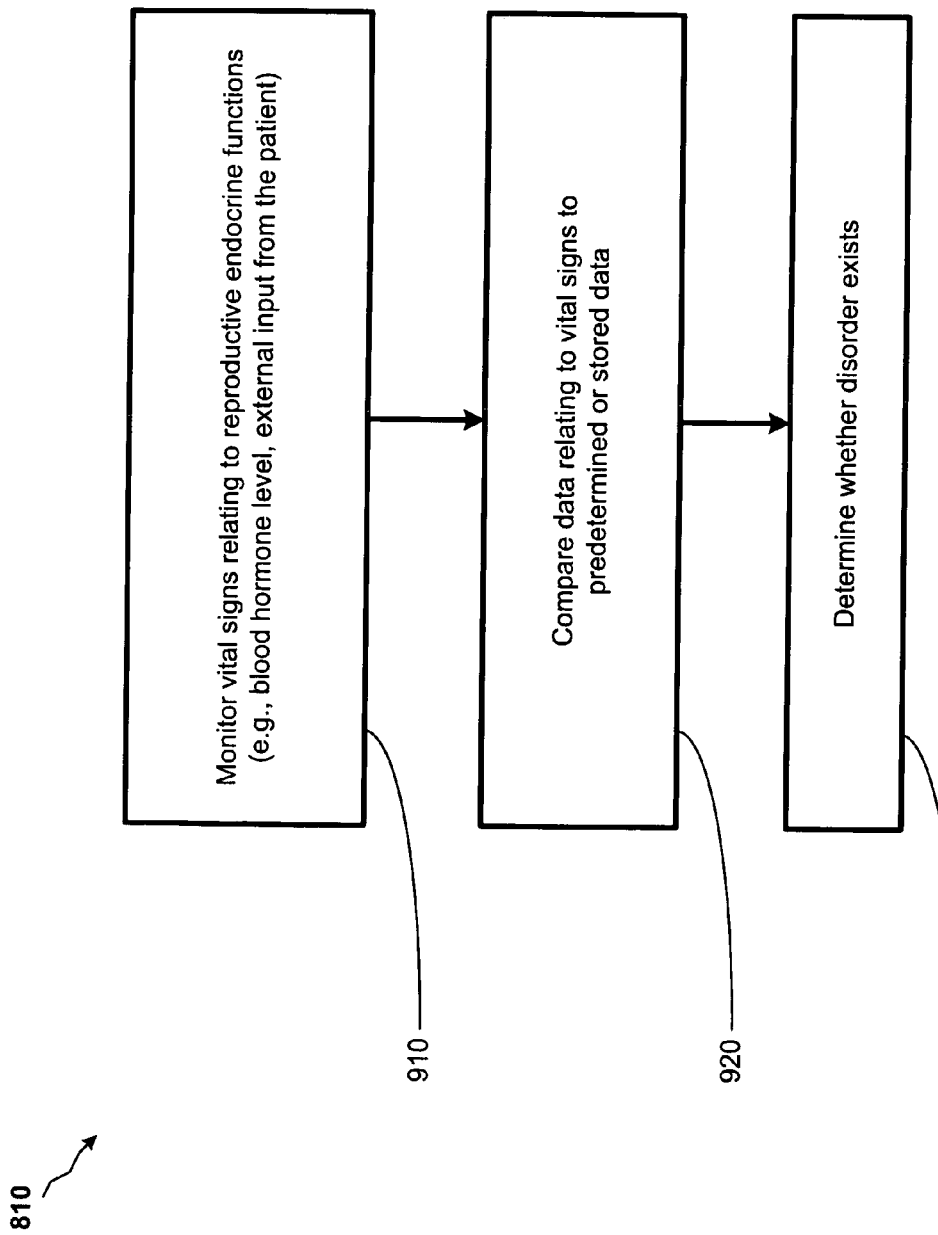
FIG. 8 depicts a more detailed flowchart depiction of the step of performing a detection process of FIG. 7, in accordance with an illustrative embodiment of the present invention.

Turning now to FIG. 8, a more detailed block diagram depiction of the step of performing the detection process of block 810 in FIG. 7 is illustrated. The system 100 may monitor one or more vital signs relating to the reproductive endocrine functions of the patient (block 910). For example, blood levels of at least one hormone, external input from the patient, etc., may be detected. This detection may be made by sensors residing inside the human body, which may be operatively coupled to the IMD 100. In another embodiment, these factors may be performed by external means and may be provided to the IMD 100 an external device via the communication system 660.

Upon acquisition of various vital signs, a comparison may be performed comparing the data relating to the vital signs to predetermined, stored data (block 920). For example, the hormone level(s) may be compared to various predetermined thresholds to determine whether aggressive action would be needed, or simply further monitoring would be sufficient. Based upon the comparison of the collected data with theoretical, stored thresholds, the IMD 100 may determine whether a disorder exists (block 930). For example, various vital signs may be acquired in order to determine whether afferent or efferent fibers are to be stimulated. Based upon the determination described in FIG. 8, the IMD 100 may continue to determine whether the disorder is sufficiently significant to perform treatment, as described in FIG. 7.

Figure 9:
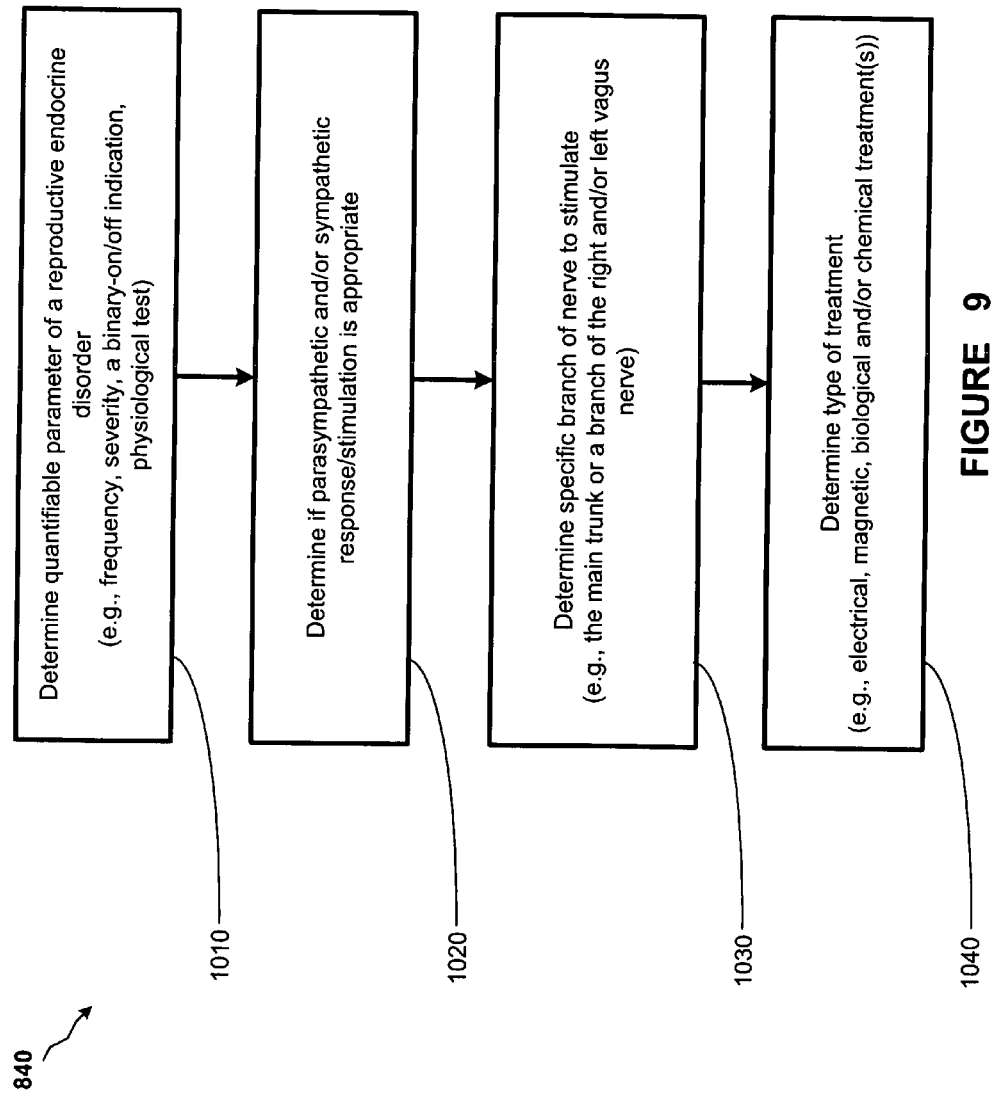
FIG. 9 depicts a more detailed flowchart depiction of the steps of determining a particular type of stimulation based upon data relating to a reproductive endocrine disorder described in FIG. 7, in accordance with an illustrative embodiment of the present invention.

Turning now to FIG. 9, a more detailed flowchart depiction of the step of determining the type of stimulation indicated in block 840 of FIG. 7 is illustrated. The IMD 100 may determine a quantifiable parameter of a reproductive endocrine disorder (block 1010). These quantifiable parameters, for example, may include a frequency of occurrence of various symptoms of a reproductive endocrine disorder, among others. Based upon these quantifiable parameters, a determination may be made whether a parasympathetic or a sympathetic response/stimulation is appropriate (block 1020). For example, as illustrated in Table 2, a matrix may be used to determine whether a parasympathetic or a sympathetic response for stimulation is appropriate. This determination may be overlaid by the decision regarding whether an efferent, an afferent, or an efferent-afferent combination stimulation should be performed.

TABLE 2

|  | EFFERENT | AFFERENT | EFFERENT-AFFERENT |
|---|---|---|---|
| PARASYMPATHETIC | Yes | No | No |
| SYMPATHETIC | Yes | Yes | Yes |

The example illustrated in Table 2 shows that an efferent, parasympathetic stimulation may be provided in combination with a sympathetic, efferent-afferent combination stimulation for a particular treatment. A determination may be made that for a particular type of quantifiable parameter that is detected, the appropriate treatment may be to perform a parasympathetic blocking signal in combination with a sympathetic non-blocking signal. Other combinations relating to Table 2 may be implemented for various types of treatments. Various combinations of matrix, such as the matrix illustrated in Table 2 may be stored in the memory for retrieval by the IMD 100.

Additionally, external devices may perform such calculation and communicate the results or accompanying instructions to the IMD 100. The IMD 100 may also determine the specific batch of the nerve to stimulate (block 1030). For example, for a particular type of stimulation to be performed, the decision may be made to stimulate the main trunk of the right or left vagus nerve or a branch thereof. The IMD 100 may also indicate the type of treatment to be delivered. For example, an electrical treatment alone or in combination with another type of treatment may be provided based upon the quantifiable parameter(s) that are detected (block 1040). For example, a determination may be made that an electrical signal by itself is to be delivered. Alternatively, based upon a particular type of disorder, a determination may be made that an electrical signal, in combination with a magnetic signal, such as transcranial magnetic stimulation (TMS) may be delivered. Stimulation can be induced by light such as from a laser.

In addition to electrical or magnetic stimulation, a determination may be made whether to deliver a chemical, biological, or other type of treatment(s) in combination with the electrical stimulation provided by the IMD 100. In one example, electrical stimulation may be used to enhance the effectiveness of a chemical agent, such as hormone-replacement drug. Therefore, various drugs or other compounds may be delivered in combination with an electrical stimulation or a magnetic stimulation. Based upon the type of stimulation to be performed, the IMD 100 delivers the stimulation to treat various reproductive endocrine disorders.

Using embodiments of the present invention, various types of stimulation may be performed to treat reproductive endocrine disorders, such as gonadal dysgenesis, hypogonadism, hypergonadism, delayed puberty, amenorrhea, infertility, premature menopause, and polycystic ovarian disease. The autonomic stimulation of embodiments of the present invention may include stimulation of the portions of a vagus nerve or sympathetic nerves. Embodiments of the present invention provide for performing preprogrammed delivery of stimulation or performing real time decision-making to deliver controlled stimulation. For example, various detections of parameters, such as factors relating to a reproductive endocrine disorder, may be used to determine whether a stimulation is needed or the type of stimulation that is to be delivered. Parasympathetic, sympathetic, blocking, non-blocking, afferent, or efferent delivery of stimulation may be performed to treat various reproductive endocrine disorders.

All of the methods and apparatus disclosed and claimed herein may be made and executed without undue experimentation in light of the present disclosure. While the methods and apparatus of this invention have been described in terms of particular embodiments, it will be apparent to those of skill in the art that variations may be applied to the methods and apparatus and in the steps or in the sequence of steps of the method described herein without departing from the concept, spirit and scope of the invention as defined by the appended claims. It should be especially apparent that the principles of the invention may be applied to selected cranial nerves other than the vagus nerve to achieve particular results.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method of treating a reproductive disorder in a patient, comprising:
coupling at least one electrode to at least one portion of a cranial nerve of the patient, wherein said cranial nerve is selected from the group consisting of a vagus nerve, a trigeminal nerve, an accessory nerve, or a hypoglossal nerve; and
applying an electrical signal to said cranial nerve using said electrode to treat said reproductive disorder, wherein treating said reproductive disorder comprises treating a disorder selected from the group consisting of infertility and amenorrhea.

2. The method of claim 1, wherein the cranial nerve is a vagus nerve.

3. The method of claim 1, wherein treating said reproductive disorder comprises treating a disorder selected from the group consisting of gonadal dysgenesis, hypogonadism, hypergonadism, delayed puberty, amenorrhea, infertility, premature menopause, polycystic ovarian syndrome, osteoporosis, hirsutism, and sarcopenia.

4. The method of claim 1, wherein applying said electrical signal comprises applying said electrical signal in synchronization with a normal endogenous endocrine cycle.

5. The method of claim 1, further comprising detecting a symptom of the reproductive disorder, and wherein applying the electrical signal is initiated in response to detecting said symptom.

6. The method of claim 1, wherein applying the electrical signal comprises applying said signal to the cranial nerve using said at least one electrode during a first treatment period, and said method further comprises applying a second electrical signal to the cranial nerve using said at least one electrode during a second treatment period, to treat the reproductive disorder.

7. The method of claim 1, wherein applying the electrical signal comprises blocking one of afferent and efferent action potentials on the cranial nerve.

8. The method of claim 1, further comprising the steps of:
providing a programmable electrical signal generator;
coupling said signal generator to said at least one electrode;
generating an electrical signal with the electrical signal generator; and
applying the electrical signal to the electrode.

9. The method of claim 8, further comprising programming the electrical signal generator to define the electrical signal by at least one parameter selected from the group consisting of a current magnitude, a pulse frequency, a pulse width, an on-time and an off-time, wherein said at least one parameter is selected to treat the reproductive disorder.

10. The method of claim 9, further comprising detecting one or more of the period or the amplitude of an endocrine cycle associated with the reproductive endocrine disorder, and wherein the parameter of the electrical signal is modified in response to detecting said period or said amplitude.

11. The method of claim 1, wherein applying an electrical signal to said cranial nerve comprises applying an electrical signal from a medical device selected from the group consisting of an implantable medical device, an external medical device, and a partially implantable medical device.

12. A method of treating a reproductive endocrine disorder in a patient, comprising:
coupling at least one electrode to at least a portion of a cranial nerve of the patient, wherein said cranial nerve is selected from the group consisting of a vagus nerve, a trigeminal nerve, an accessory nerve, or a hypoglossal nerve;
receiving a signal indicative of a symptom of the reproductive endocrine disorder; and
applying an electrical signal to said cranial nerve using said electrode to treat said reproductive endocrine disorder in response to receiving said signal indicative of said symptom, wherein applying said electrical signal comprises applying said electrical signal in synchronization with at least one endogenous endocrine cycle.

13. The method of claim 12, wherein applying the electrical signal comprises applying said signal to the cranial nerve using said at least one electrode during a first treatment period, and said method further comprises applying a second electrical signal to the cranial nerve using said at least one electrode during a second treatment period, to treat the reproductive endocrine disorder.

14. The method of claim 12, wherein treating said reproductive endocrine disorder comprises treating a disorder selected from the group consisting of gonadal dysgenesis, hypogonadism, hypergonadism, delayed puberty, amenorrhea, infertility, premature menopause, and polycystic ovarian disease.

15. The method of claim 12, further comprising:
providing a drug delivery device in fluid communication with the bloodstream of the patient; and
releasing from said drug delivery device a drug capable of treating said reproductive endocrine disorder in response to receiving said signal indicative of said symptom.

16. The method of claim 15, wherein releasing a drug comprises releasing a drug selected from the group consisting of follicle stimulating hormone (FSH), luteinizing hormone (LH), human chorionic gonadotropin (hCG), a luteinizing hormone-releasing hormone (LHRH) agonist, an estrogen, an anti-androgen, selective estrogen reuptake modulators, a hormone replacement therapy drug, oxytocin, and a steroid.

17. The method of claim 15, wherein treating said reproductive endocrine disorder comprises treating a disorder selected from the group consisting of gonadal dysgenesis, hypogonadism, hypergonadism, delayed puberty, amenorrhea, infertility, premature menopause, and polycystic ovarian disease.

18. The method of claim 15, further comprising:
applying a first signal to said drug delivery device to release said drug during a first time period;
receiving a second indication of a symptom of the reproductive endocrine disorder subsequent to delivery of said drug;
applying said electrical signal to said portion of said cranial nerve during a second time period in response to said receiving said second indication of a symptom of the reproductive endocrine disorder.

19. An implantable medical device system, comprising:
an electrode adapted to be coupled to a cranial nerve of a patient, wherein said cranial nerve is selected from the group consisting of a vagus nerve, a trigeminal nerve, an accessory nerve, or a hypoglossal nerve, and
an implantable medical device for treating at least one reproductive disorder in a patient, comprising a controller for providing an electrical signal to the electrode, to treat said reproductive disorder, wherein treating said reproductive disorder comprises treating a disorder selected from the group consisting of and amenorrhea.

20. The implantable medical device of claim 19, further comprising:
   a sensor for sensing a symptom of the reproductive disorder; and
   wherein said controller receives a sensor signal from said sensor indicative of said symptom, and provides said electrical signal to said electrode in response to receiving said sensor signal.

21. An implantable medical device system, comprising:
   an electrode adapted to be coupled to a cranial nerve of a patient, wherein said cranial nerve is selected from the group consisting of a vagus nerve, a trigeminal nerve, an accessory nerve, or a hypoglossal nerve, and
   an implantable medical device for treating at least one reproductive disorder in a patient, comprising a controller for providing an electrical signal to the electrode for treating said reproductive endocrine disorder, wherein treating said reproductive disorder comprises treating a disorder selected from the group consisting of gonadal dysgenesis, hypogonadism, hypergonadism, delayed puberty, amenorrhea, infertility, premature menopause, polycystic ovarian syndrome, osteoporosis, hirsutism, and sarcopenia.

22. A method of treating a reproductive disorder in a patient, comprising:
   coupling at least one electrode to at least one portion of a cranial nerve of the patient, wherein said cranial nerve is selected from the group consisting of a vagus nerve, a trigeminal nerve, an accessory nerve, or a hypoglossal nerve; and
   applying an electrical signal to said cranial nerve using said electrode to treat said reproductive disorder, wherein said electrical signal is applied in synchronization with said at least one endogenous endocrine cycle.

* * * * *

UNITED STATES PATENT AND TRADEMARK OFFICE
CERTIFICATE OF CORRECTION

PATENT NO.        : 7,657,310 B2                                           Page 1 of 1
APPLICATION NO.   : 11/340309
DATED             : February 2, 2010
INVENTOR(S)       : William R. Buras It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 47 days.

Signed and Sealed this

Thirtieth Day of November, 2010

David J. Kappos
*Director of the United States Patent and Trademark Office*